US012758208B2

(12) United States Patent
Anderson

(10) Patent No.: US 12,758,208 B2
(45) Date of Patent: Oct. 13, 2026

(54) SUTURE BUTTON AND METHODS

(71) Applicant: INS Ortho, Inc., Providence, RI (US)

(72) Inventor: Christian N. Anderson, Nashville, TN (US)

(73) Assignee: INS Ortho, Inc., Providence, RI (US)

( * ) Notice: Subject to any disclaimer, the term of this patent is extended or adjusted under 35 U.S.C. 154(b) by 0 days.

(21) Appl. No.: 18/439,038

(22) Filed: Feb. 12, 2024

(65) Prior Publication Data

US 2024/0268812 A1 Aug. 15, 2024

Related U.S. Application Data

(60) Provisional application No. 63/444,978, filed on Feb. 12, 2023, provisional application No. 63/444,976, filed on Feb. 12, 2023.

(51) Int. Cl.
*A61B 17/04* (2006.01)
*A61F 2/08* (2006.01)

(52) U.S. Cl.
CPC ...... *A61B 17/0401* (2013.01); *A61B 17/0466* (2013.01); *A61F 2/0811* (2013.01); *A61B 2017/0404* (2013.01); *A61B 2017/0414* (2013.01); *A61B 2017/0458* (2013.01); *A61B 2017/0459* (2013.01); *A61B 2017/0464* (2013.01); *A61F 2002/0823* (2013.01);
(Continued)

(58) Field of Classification Search
CPC .............................................. A61B 2017/0404
See application file for complete search history.

(56) References Cited

U.S. PATENT DOCUMENTS 5,306,301 A * 4/1994 Graf ...................... A61F 2/0805
623/13.12
6,042,609 A * 3/2000 Giordano .............. A61F 2/0811
424/423
(Continued)

FOREIGN PATENT DOCUMENTS

WO 2020047174 A1 3/2020

OTHER PUBLICATIONS

International Search Report and Written Opinion issued in related Application Serial No. PCT/US2024/015406 on Jun. 26, 2024.

*Primary Examiner* — Shaun L David
(74) *Attorney, Agent, or Firm* — Holland & Knight LLP; Matthew C. Cox; Forrest S. Tinnin

(57) ABSTRACT

A suture button includes a body having first and second ends and first and second sides between the respective ends. Shoulders extend from each side of the body near the respective ends. A first recess is defined between the first and second shoulders on the first side, and a second recess is defined between the first and second shoulders on the second side. Each recess narrows toward its midpoint to receive a suture strand around the body in a loop or a hitch. The shoulders on each end of each recess prevents the suture material, once tightened around the body, from inadvertently slipping off the button. A center passage through the button accommodates passage of one or more suture constructs for ligament fixation and/or internal bracing. One or more holes are defined through the button between the center passage and one or both ends of the button in some embodiments.

19 Claims, 24 Drawing Sheets

(52) U.S. Cl.
CPC ................. *A61F 2002/0852* (2013.01); *A61F 2002/0858* (2013.01); *A61F 2002/0882* (2013.01)

(56) References Cited

U.S. PATENT DOCUMENTS 6,063,106 A * 5/2000 Gibson .............. A61B 17/0401 606/232
2005/0288711 A1* 12/2005 Fallin ................. A61B 17/0401 606/232
2006/0190041 A1* 8/2006 Fallin ................. A61B 17/0487 606/232
2007/0233241 A1* 10/2007 Graf ................... A61B 17/0401 623/13.14
2008/0046009 A1* 2/2008 Albertorio ......... A61B 17/0401 606/232
2009/0281563 A1* 11/2009 Newell ............ A61B 17/07207 606/191
2010/0125297 A1* 5/2010 Guederian ......... A61B 17/0401 606/232
2010/0268273 A1* 10/2010 Albertorio ......... A61B 17/0487 606/232
2011/0087280 A1* 4/2011 Albertorio ............ A61F 2/0811 606/232
2011/0125189 A1* 5/2011 Stoll, Jr. ............ A61B 17/0401 606/232
2011/0160856 A1* 6/2011 Sinnott ................. A61F 2/0811 623/13.14
2012/0046747 A1* 2/2012 Justin ................. A61B 17/0401 606/232
2012/0065731 A1* 3/2012 Justin .................... A61F 2/0811 623/13.14
2012/0150203 A1* 6/2012 Brady ................... A61F 2/0811 606/148
2013/0035720 A1* 2/2013 Perriello ............... A61F 2/0811 606/232
2013/0172944 A1* 7/2013 Fritzinger .......... A61B 17/0401 606/232
2015/0039026 A1* 2/2015 Pasquali .......... A61B 17/06166 606/228
2015/0094761 A1* 4/2015 Spenciner ............. A61F 2/2846 606/232
2015/0157449 A1* 6/2015 Gustafson .......... A61B 17/0401 606/232
2015/0196385 A1* 7/2015 Kam .................. A61B 17/0401 623/13.14
2016/0113755 A1* 4/2016 Senior ................... A61F 2/0805 623/13.14
2016/0270776 A1* 9/2016 Miraki ............... A61B 17/0487
2018/0271522 A1* 9/2018 Medoff .............. A61B 17/0401
2019/0008502 A1* 1/2019 Anderson .......... A61B 17/0401
2019/0143001 A1* 5/2019 Lin ......................... A61L 27/54 623/23.75
2022/0168092 A1 6/2022 Anderson

* cited by examiner

SUTURE BUTTON AND METHODS

CROSS-REFERENCE TO RELATED APPLICATIONS

This application claims benefit of and priority to U.S. provisional application 63/444,976 filed Feb. 12, 2023 entitled Suture Button and Methods, all of which is hereby incorporated by reference in its entirety. This application also claims benefit of and priority to U.S. provisional application 63/444,978 filed Feb. 12, 2023 entitled Static Internal Brace Devices and Methods, all of which is hereby incorporated by reference in its entirety.

TECHNICAL FIELD

The present disclosure relates to devices and methods for orthopedic surgery, and more particularly to suture fixation devices for repair and reconstruction of ligaments and tissue.

BACKGROUND

Conventional devices and methods for repair and reconstruction of ligaments and tissue include flexible sutures that may be attached to tissue and anchored to surrounding tissue or bone to place the tissue in an anatomically correct position to facilitate healing and growth. Conventional fixation devices include rigid anchors for securing a suture to an anchor point such that the suture can be pulled tight against bone or tissue. Conventional fixation devices include suture buttons or screws which may be disposed at the distal end of a suture construct and placed against bone or tissue to provide an anchor point. Some conventional fixation devices are difficult to deploy in the surgical field and are inadequate for conveniently securing suture material to the fixation device, particularly at the opening orifice of a drilled bone tunnel or socket.

Another problem with conventional suture fixation devices are the use of separate anchors for ligament fixation and internal bracing, especially in orthopedic surgery of joints. Conventional devices and methods may require using a first anchor for an internal mechanical brace, and a separate anchor for a ligament fixation suture construct. Such use of multiple anchors can lead to additional complexity during surgery, additional expense, extended operation time, enhanced wear or crowding at the anchor site, or other problems leading to loosening of the suture constructs over time. Additionally, conventional suture anchors for ligament fixation or internal bracing may not be configured for smooth passage through a trans-osseous bone tunnel. What is needed then, are improvements in suture fixation devices and methods.

BRIEF SUMMARY

The present disclosure provides devices and methods for fixation of suture material when repairing or reconstructing ligaments in humans and animals, including but not limited to repair or reconstruction of the anterior cruciate ligament (ACL), posterior cruciate ligament (PCL), medial collateral ligament (MCL), medial or lateral meniscus, biceps tendon, quadriceps tendon, or other anatomical features in the various joints in humans and animals for repair or reconstruction during orthopedic surgery. In some embodiments, the suture button of the present disclosure provides a fixation device configured for use in static or dynamic repair of the ACL.

In some embodiments, the present disclosure includes a suture button including a body having a tapered first end and a second tapered end. Each tapered end includes a convex profile having a convex radius and first and second shoulders disposed on each end. The curved radius of the shoulders provides both enhanced passage of suture material over the shoulders and also enhanced travel of the suture button through tissue or a bone tunnel. A first recess is defined in the first side, and a second recess is defined in the second side. Each recess includes a radius narrowing to a midpoint along the lateral centerline of the button. A center passage is defined in the body between the first and second ends. A first hole is defined in the body between the center passage and the first end, and a second hole is defined in the body between the center passage and the second end. The center passage is defined to accommodate passage of a loop on suture material such that the loop may be passed over the first or second end to secure the loop on the body in a looped hitch. The center passage includes a length greater than its width in some embodiments.

In further embodiments, the present disclosure provides a body as described above including a bridge spanning the center passage. The bridge cradles suture material passing on either side of the bridge through a first passage on one side of the bridge and a second passage on the opposite side of the bridge. As such, the suture button can be attached to a fixed or free loop on a suture construct.

In further embodiments, the present disclosure provides a suture button configured to anchor both a ligament fixation suture construct and an internal brace suture construct.

In additional embodiments, the present disclosure provides a suture button configured for passage through a bone tunnel via a passing suture while carrying both a ligament fixation suture construct and an internal brace suture construct secured to the suture button.

In additional embodiments, the present disclosure provides a suture button configured for use with a self-cinching ligament fixation suture construct.

Yet another objective of the present disclosure is to provide a suture button that may be used for performing repair of the anterior cruciate ligament (ACL).

Another object of the present disclosure is to provide a suture button that may be used in combination with both an internal brace and a ligament fixation suture construct as a dual-purpose anchor.

Numerous other objects, advantages and features of the present disclosure will be readily apparent to those of skill in the art upon a review of the drawings and description as set forth below.

DETAILED DESCRIPTION

Figure 1:
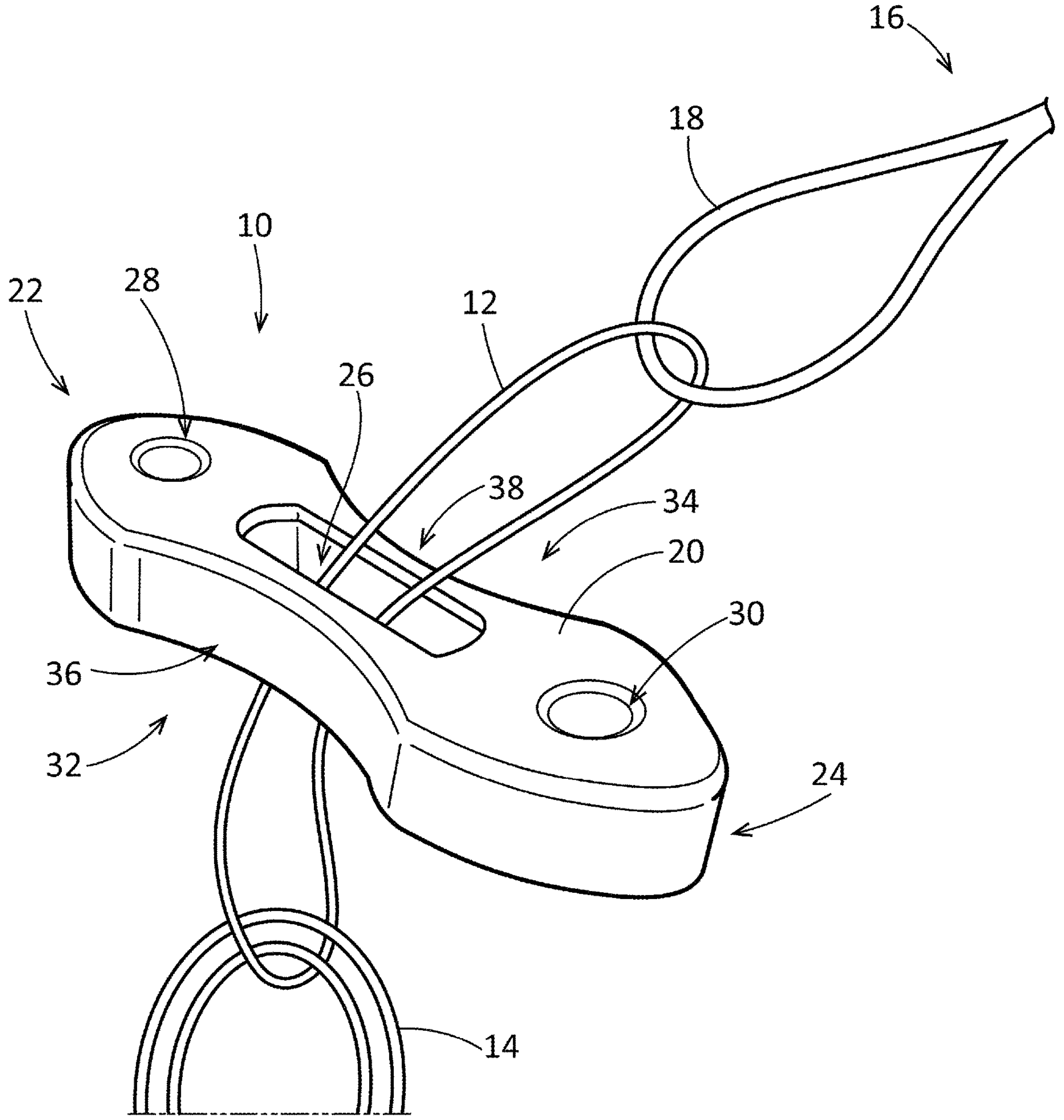
FIG. 1 illustrates a perspective view of an embodiment of a button including a suture construct extending through the center passage in position for attachment to the button.

Referring to FIG. 1, the present disclosure in some embodiments provides a suture button 10 shaped to accommodate suture material during orthopedic surgery. The suture button 10 is sized and shaped to be used during various types of procedures to secure a suture construct such to bone or tissue, particularly at the distal end of a drilled bone tunnel. Suture button 10 includes a body 20 comprising any suitable rigid material, such as but not limited to metal, polymer, composite, titanium, steel, etc. known in the art for suture buttons.

Figure 3:
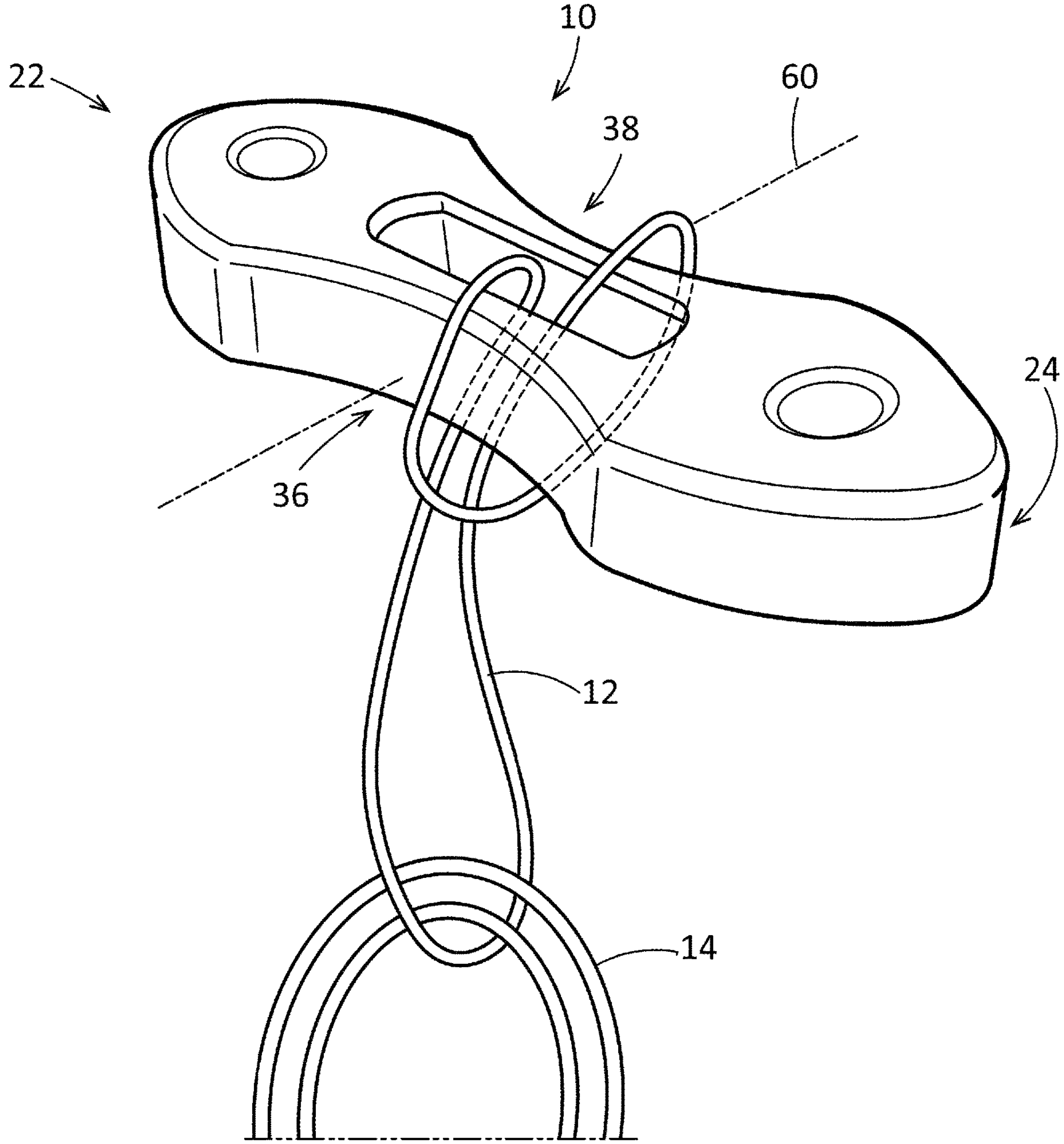
FIG. 3 illustrates a perspective view of an embodiment of a button including a suture construct extending through the center passage and secured to the button.

Suture button 10 is configured for attachment to a suture construct such as the construct illustrated in FIG. 1, including an adjustable loop 14 comprising one or more adjustable loops, a free loop 12 disposed on the adjustable loop 14 and a shuttling suture 16 including a shuttling suture fixed loop 18 attached to the free loop. Suture button 10 includes a center passage 26 positioned to receive one or more strands of suture material. In some embodiments, shuttling suture 16 is passed through center passage 26 such that center passage 26 is aligned with free loop 12. From this position, as shown in FIG. 3, free loop 12 may be pulled over first button end 22 or second button end 24 to form a hitch around suture button 10.

Suture button 10 is specifically configured to accommodate a loop being placed over first or second button ends 22, 24 by providing a tapered first button end 22 and a tapered second button end 24. Each tapered button end 22, 24 includes a convex radius. As such, free loop 12 may be slid over either first button end 22 or second button end 24.

Suture button 10 also includes a first side 32 and a second side 34. Suture button 10 includes a longitudinal dimension between first and second button ends 22, 24 greater than the lateral dimension between first side 32 and second side 34. A first recess 36 is defined in first side 32, and a second recess 38 is defined in second side 34. First and second sides 32, 34 are configured to retain the loop 12 in the first and second recesses 36, 38 after the loop is passed around first or second ends 22, 24, as shown in FIG. 3. The first recess 36 and second recess 38 each form a smooth, uninterrupted arc along its entire length on the surface of button 10 in some embodiments to prevent a suture from catching as it slides along each recess surface to the mid-point of each recess.

Suture button 10 also includes a first hole 28 defined in body 20 between first end 22 and center passage 26, and a second hole 30 is defined in body 20 between second end 24 and center passage 26. First and second holes 28, 30 are positioned to accept a passing suture that may be temporarily secured to button 10 to pull the button 10 through a drilled bone tunnel or through tissue such that the button 10 is pulled through the tunnel from a longitudinal end. This configuration allows suture button 10 to be pulled axially through a drilled bone tunnel while the free or fixed loop is hitched around the body. Each of first and second holes 28, 30 are positioned to optimize pulling suture button through a drilled bone tunnel or through tissue.

Figure 2:
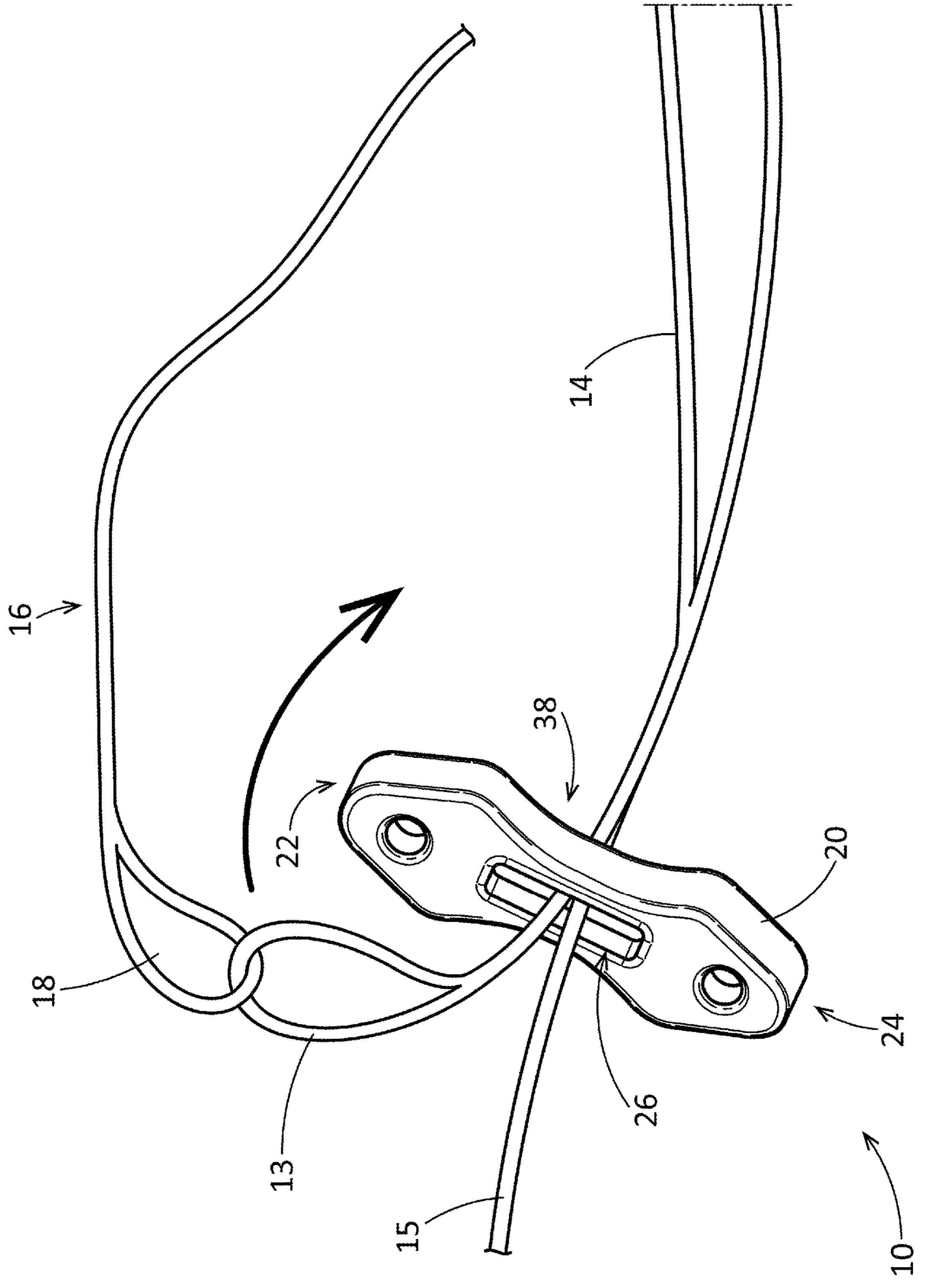
FIG. 2 illustrates a perspective view of an embodiment of a button including a suture construct extending through the center passage in position for attachment to the button.
Figure 4:
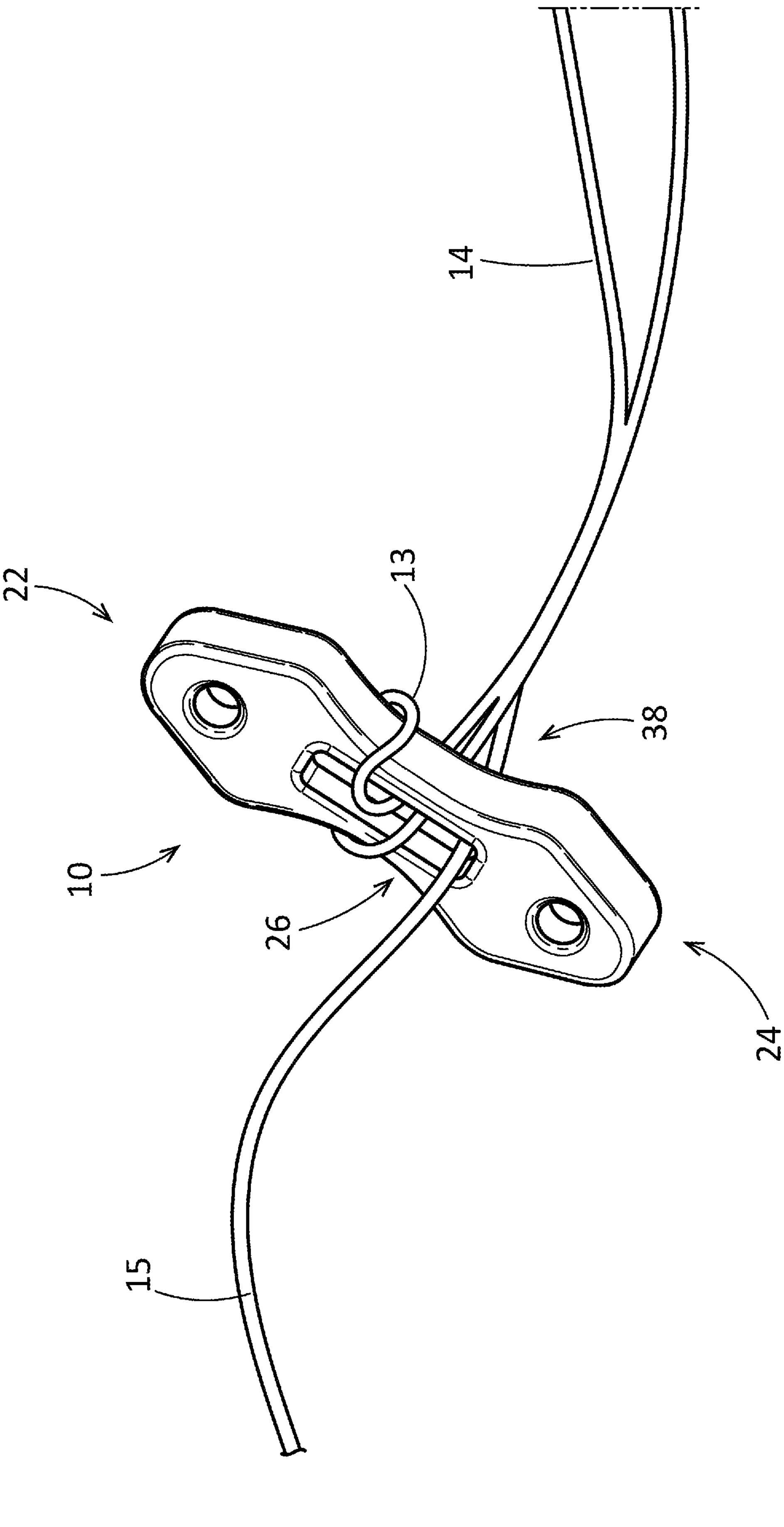
FIG. 4 illustrates a perspective view of an embodiment of a button including a suture construct extending through the center passage and secured to the button.

Referring to FIG. 2, in an alternative embodiment, suture button 10 can be used to secure a fixed loop 13 on a suture construct having an adjustable loop 14 and a tag end 15. During use, the shuttling suture 16 with a shuttling suture fixed loop 18 attached to a fixed loop 13 on a suture construct can be passed through center passage 26. The tag end 15 can also be passed through center passage 26. From this position, fixed loop 13 on the suture construct can be passed over first or second end 22, 24 of the suture button 10 to form a hitch around the body 20 securing the suture construct to the suture button 10, as shown in FIG. 4. From this position, the tag end 15 can be pulled through center passage 26 to tighten adjustable loop 14. Thus, center passage 26 on suture button 10 provides two unique functions. First, center passage 26 provides passage for a loop to be passed over first or second end 22, 24. Second, center passage 26 provides a passage for a second strand such as tag end 15 to pull tension on the adjustable loop 14 of the suture construct. To achieve these functions, in some embodiments, center passage is dimensioned to accommodate multiple strands of suture material.

Referring again to FIG. 3 and FIG. 4, in some embodiments suture button 10 is configured with first recess 36 and second recess 38 each having a radius bottoming toward center passage 26 along lateral midline 60 such that the suture material of free loop 12 or fixed loop 13 such that the loop material, when hitched, is funneled toward lateral centerline 60. Such a configuration allows button 10 to be centered on a drilled bone tunnel such that the loops 12, 13 do not chafe against the edge of the bone tunnel at the orifice of the tunnel. The first and second recesses 36, 38 further operate to prevent the free loop 12 or fixed loop 14 from sliding off either first or second ends 22, 24 of the suture button 10.

Figure 5:
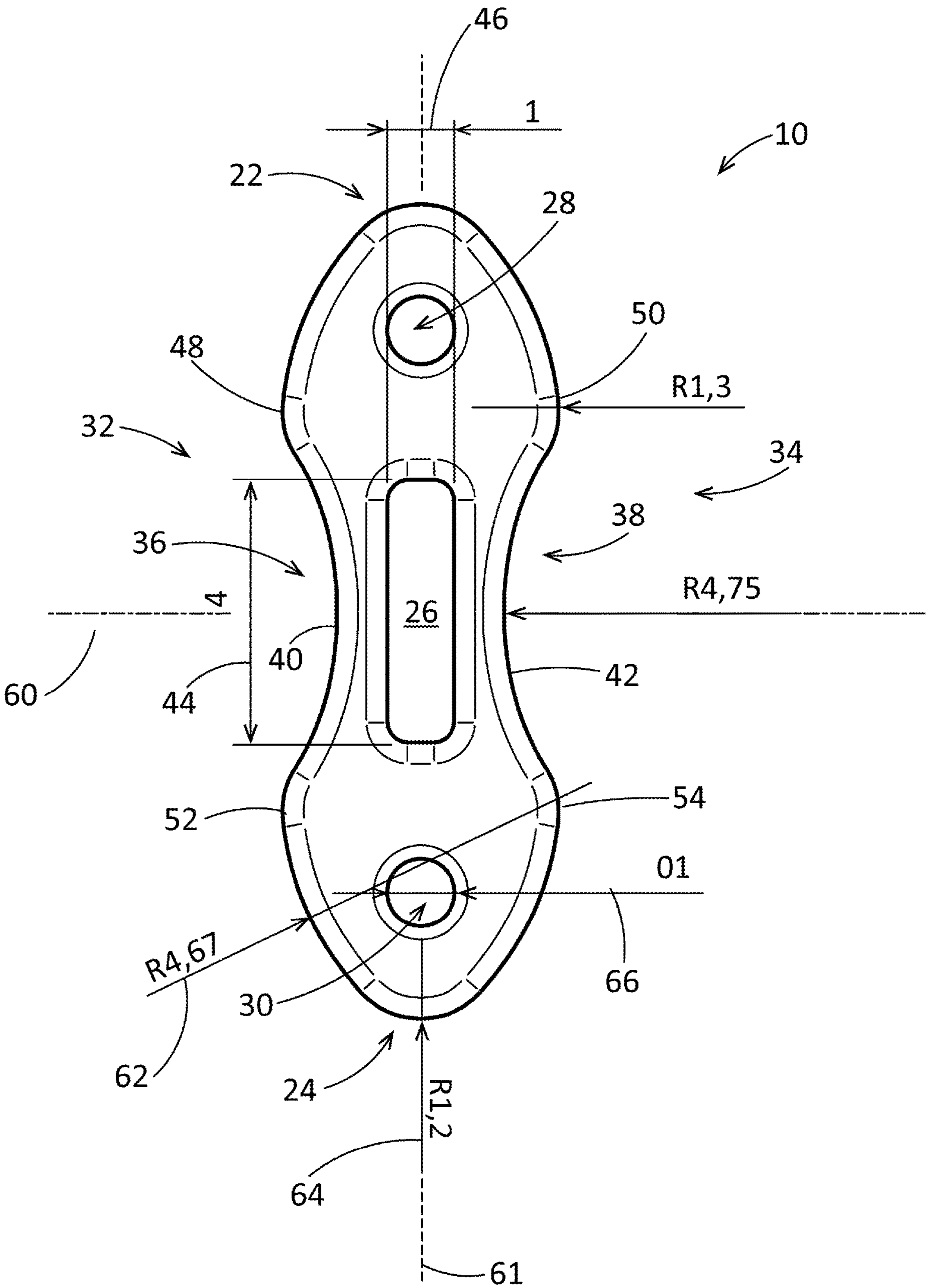
FIG. 5 illustrates a plan view of an embodiment of a button.
Figure 6:
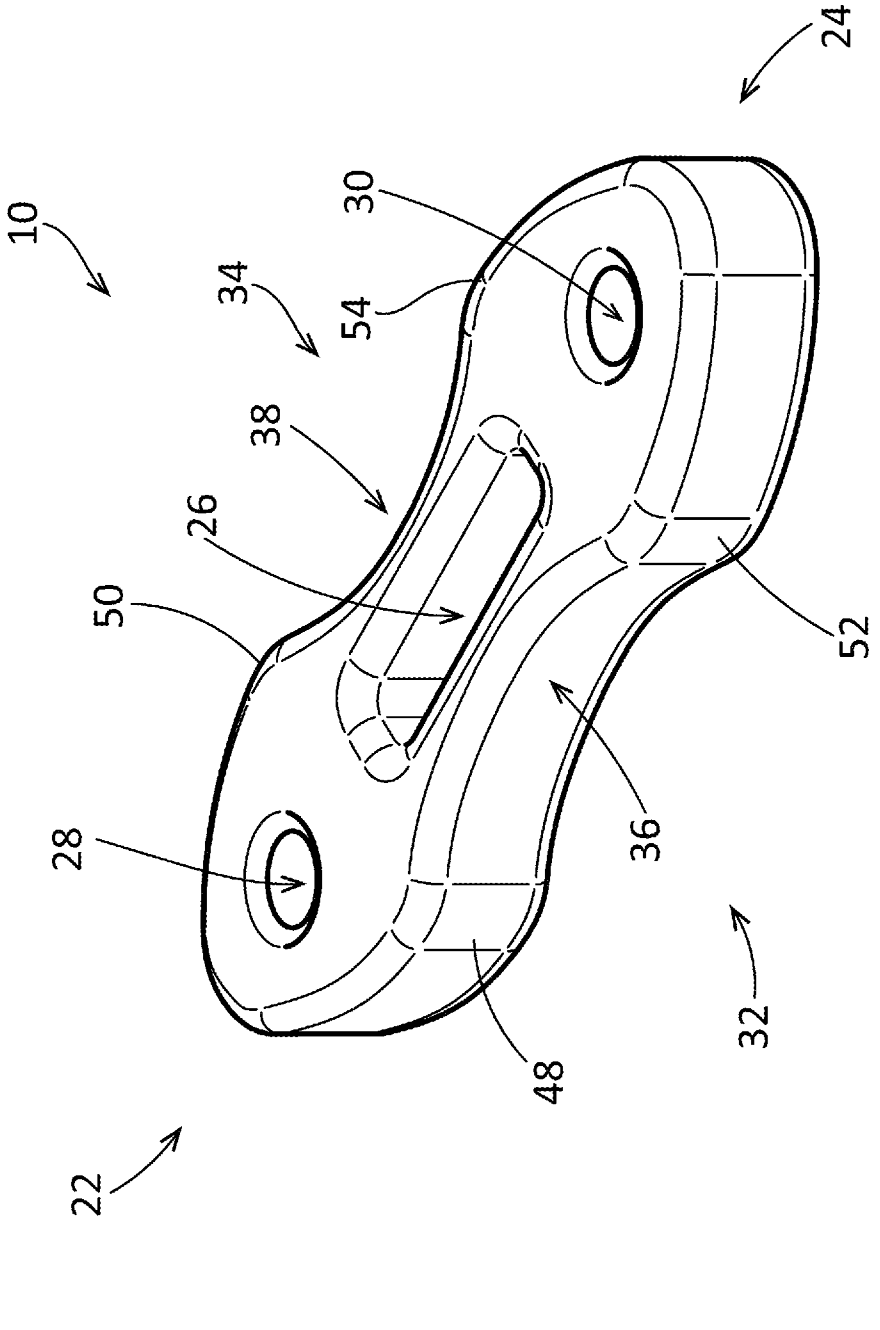
FIG. 6 illustrates a perspective view of an embodiment of a button.

Referring to FIG. 5 and FIG. 6, in some embodiments, a suture button 10 includes dimensions configured secure a suture construct. Suture button 10 includes a first end 22, a second end 24, a first side 32 and a second side 34. First end 22 and second end 24 each include a tapered profile including an end radius R1, 64 between about one and about three millimeters. In some embodiments, end radius 64 is about two millimeters for both first end 22 and second end 24. First end 22 includes a first end first shoulder 48 and a first end second shoulder 50 aligned longitudinally with each other. Second end 24 includes a second end first shoulder 52 and a second end second shoulder 54 aligned longitudinally with each other. A shoulder radius R4, 62, extends along the convex profile of first and second ends 22, 24 on both first and second sides 32, 34. Each shoulder radius 62 is between about fifty and about eighty millimeters in some embodiments. In some embodiments, shoulder radius 62 is between about sixty-five and about seventy-five millimeters. In further embodiments, shoulder radius 62 is about sixty-seven millimeters.

In some embodiments, each shoulder 48, 50, 52, 54 includes a convex radius R1 between about two millimeters and about four millimeters, and in some embodiments the convex radius R1 is about three millimeters. The curvature of each shoulder provides enhanced travel of a suture material over the shoulder toward the corresponding side recess and also provides smooth travel of the suture button 10 through a bone tunnel or tissue without catching or damaging tissue.

Referring further to FIG. 5 and FIG. 6, in some embodiments, suture button 10 includes a center passage 26 defined entirely through the suture button 10. Center passage 26 includes a center passage length 44 of between about three and about five millimeters. In further embodiments, center passage 26 includes a center passage length 44 of about four millimeters. Center passage 26 also includes a center passage width 46 less than the center passage length 44. In some embodiments, center passage width 46 is between about 0.5 mm and about 1.5 mm. In some embodiments, center passage width 46 is about one millimeter. In some embodiments, center passage length 44 is less than first side radius 40 and second side radius 42 in first and second recesses 36, 38, respectively. In some embodiments, first side radius 40 and second side radius 42 are substantially equal and are between about fifty and about one hundred millimeters. In further embodiments, first and second side radiuses 40, 42 are about seventy-five millimeters.

First hole 28 and second hole 30 each include a hole diameter 66. In some embodiments, first and second hole diameters 66 are substantially equal to center passage width 46. In some embodiments, first and second hole diameters 66 are between about 0.5 millimeters and about 1.5 millimeters. In further embodiments, first and second hole diameters 66 are about 1.0 millimeters.

In some embodiments, suture button 10 is symmetric about lateral centerline 60 and is also symmetric about longitudinal centerline 61.

Figure 7:
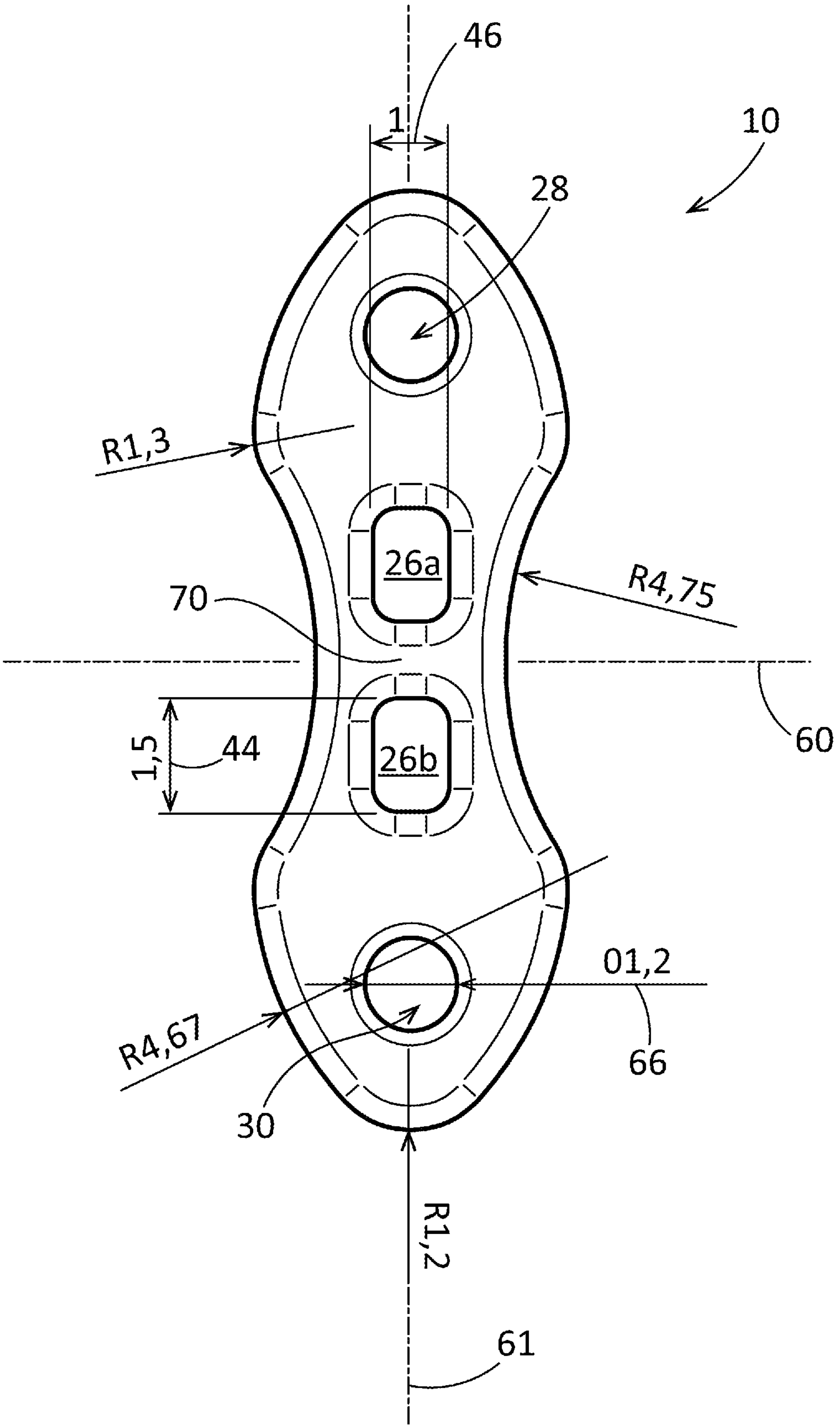
FIG. 7 illustrates a plan view of an embodiment of a button.
Figure 8:
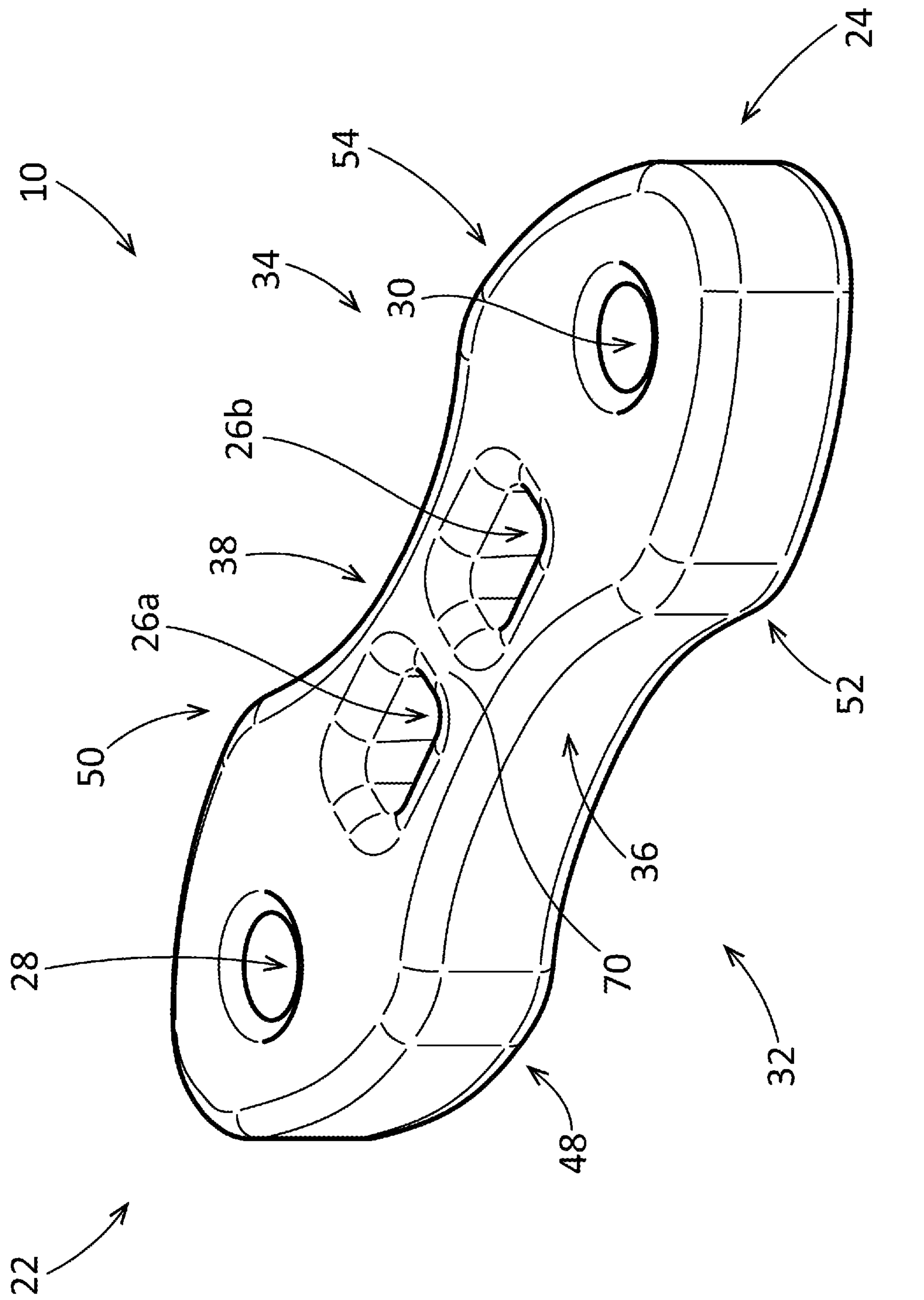
FIG. 8 illustrates a perspective view of an embodiment of a button.
Figure 9:
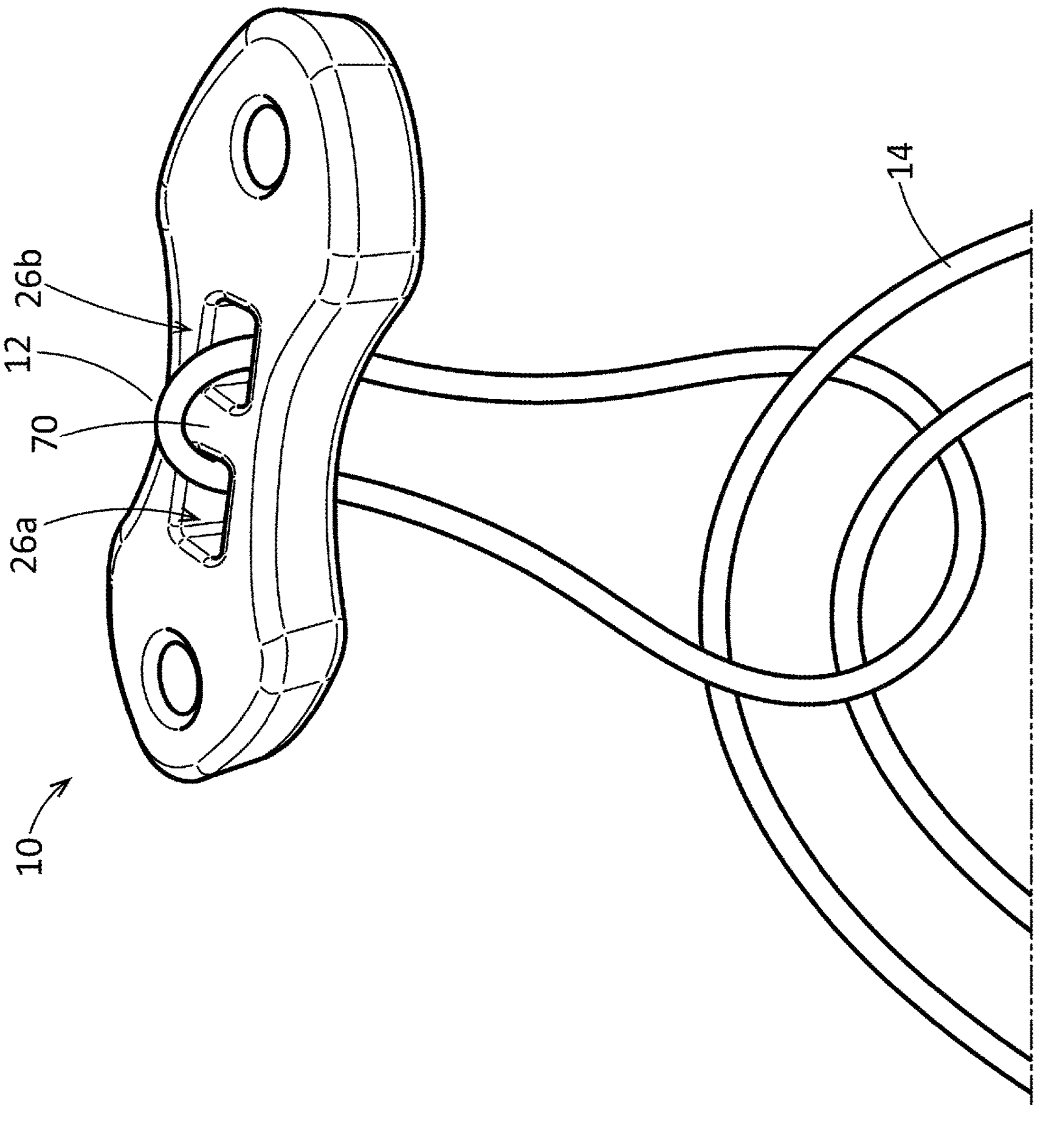
FIG. 9 illustrates a perspective view of an embodiment of a button including a suture construct extending through the center passage across a bridge secured to the button.

Referring to FIGS. 7-9, in some embodiments, suture button 10 includes an alternative configuration including a bridge 70 spanning across center passage 26, thereby bifurcating center passage 26 into a first passage **26*a* and a second passage 26*b*. Bridge 70 provides a support for a suture strand passing over bridge 70 and through first and second passages 26*a*, 26*b*, as shown in FIG. 9. First and second passages 26*a*, 26*b* each include a passage length 44 and a passage width 46. In some embodiments, each passage length 44 is between about one and about two millimeters. In further embodiments, each passage length 44 is about 1.5 millimeters. In some embodiments, each passage width 46 is between about 0.5 and about 1.5 millimeters. In further embodiments, each passage width 46 is about one millimeter. As shown in FIG. 7, in some embodiments, each hole diameter 66 of first and second holes 28, 30 are larger than the passage width 46. In some embodiment, each hole diameter 66 is between about 0.8 millimeters and about 1.5 millimeters. In further embodiments, each hole diameter 66** is about 1.2 millimeters.

Referring to the dimensions set forth in this disclosure, it will be readily appreciated by those of skill in the art that the dimensions recited herein may be scaled up or down to accommodate different applications and different suture materials. The ratios of dimensions set forth in this disclosure may be scaled accordingly to maintain similar ratios in different embodiments.

Additionally, each corner edge on suture button 10, along the outer profile on the upper and lower sides of the suture button, and also each edge on center passage 26, first and second passages **26*a*, 26*b*, first hole 28 and second hole 30**, is chamfered or has a defined radius to prevent chafing of suture material and to better facilitate smooth engagement with bone or tissue.

Figure 10:
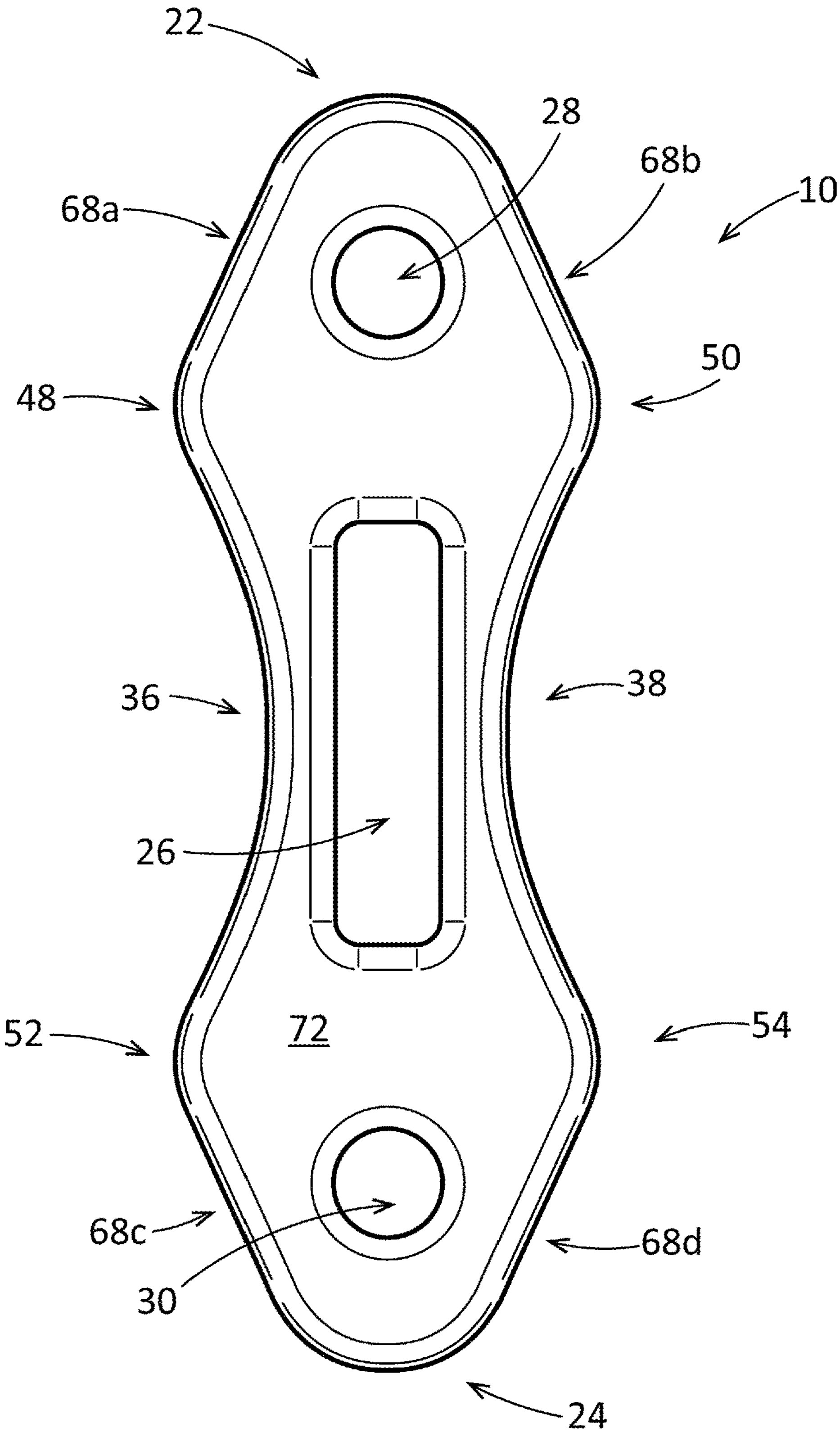
FIG. 10 illustrates a first face view of an embodiment of a button.
Figure 11:
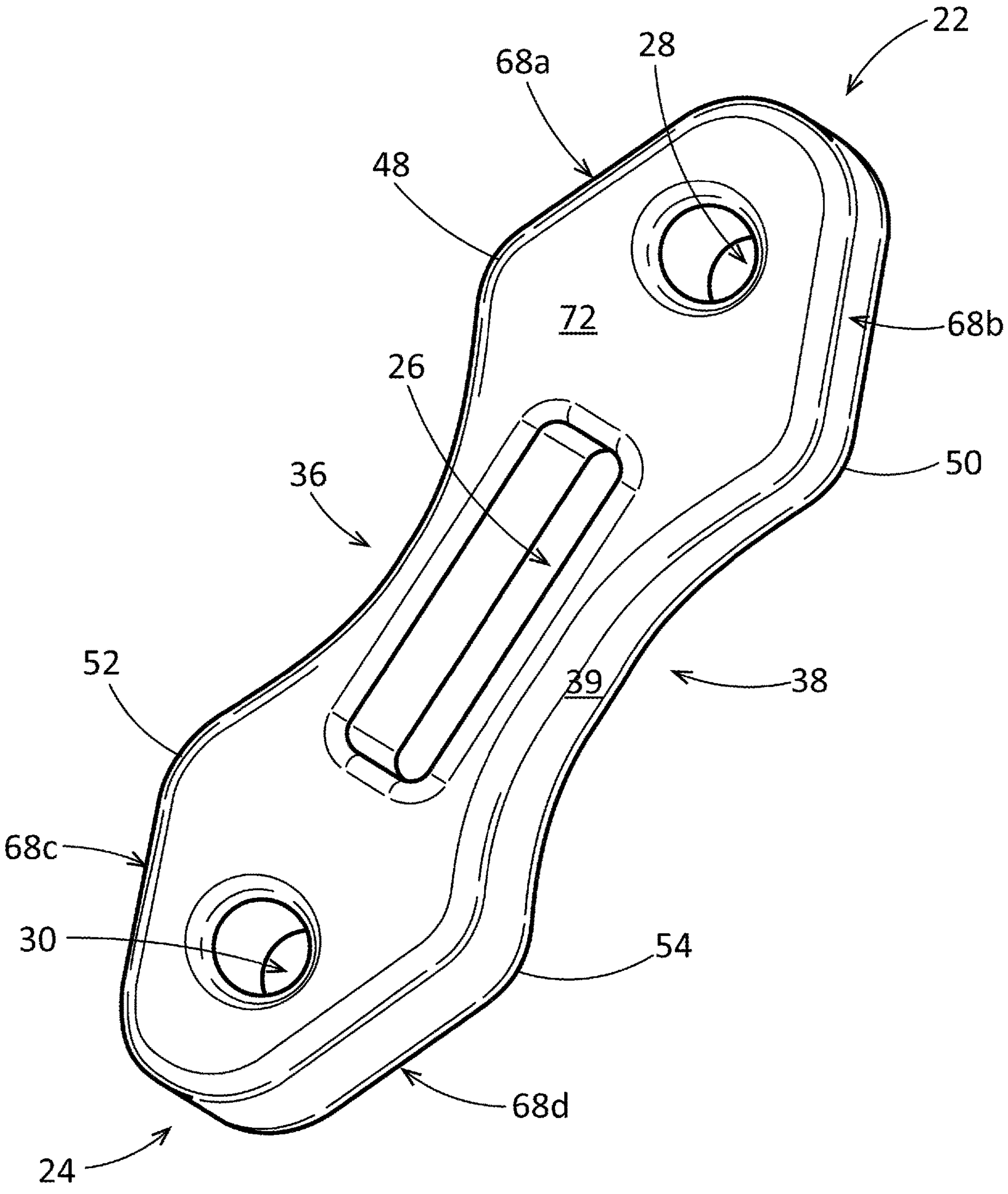
FIG. 11 illustrates a perspective view of a first face of an embodiment of a button.
Figure 12:
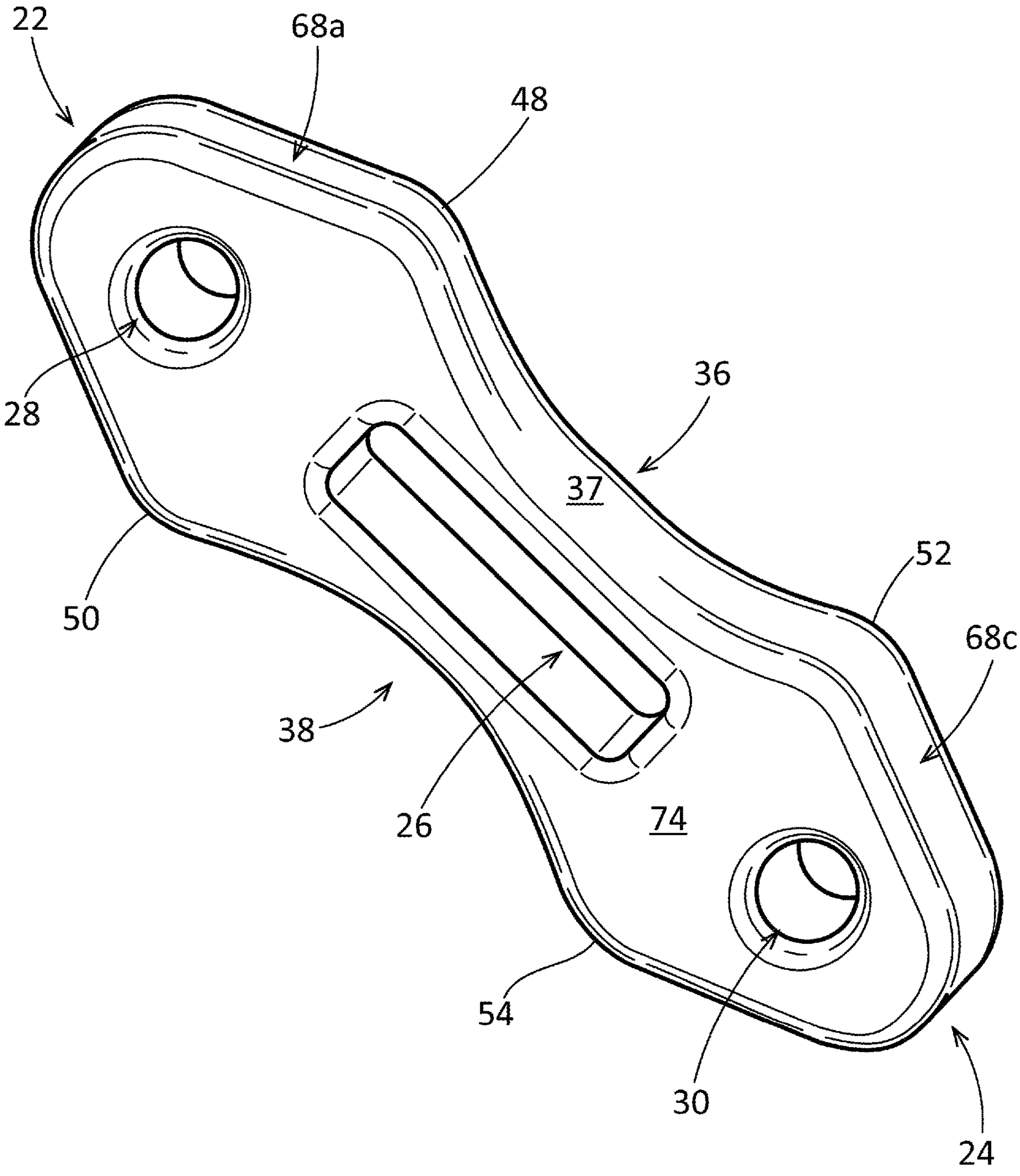
FIG. 12 illustrates a perspective view of a second face of an embodiment of a button.
Figure 13:
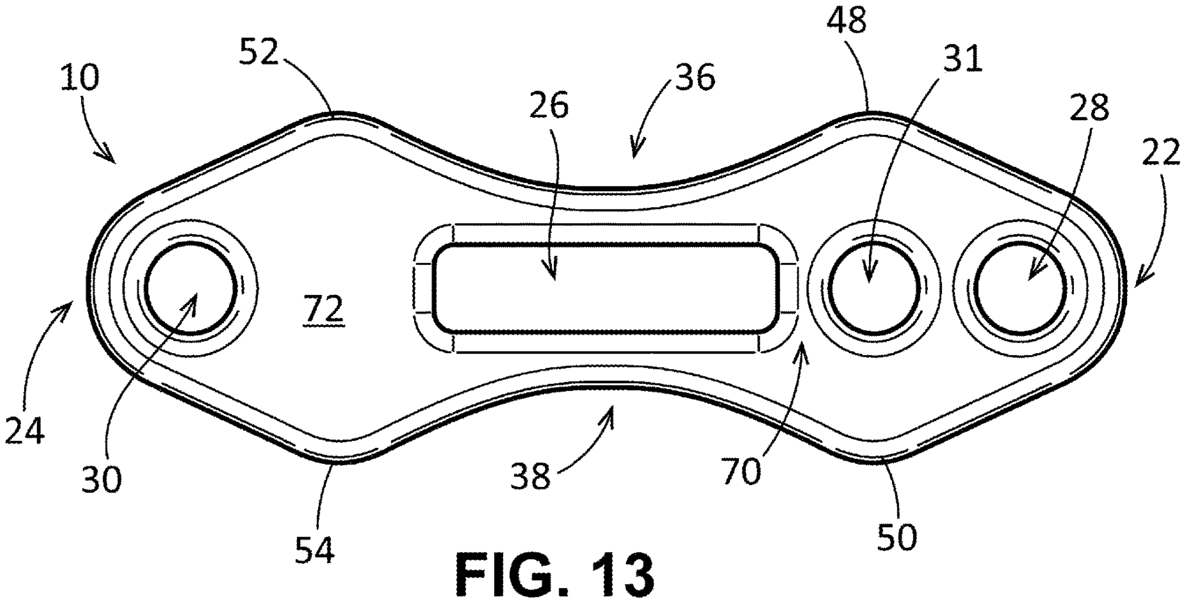
FIG. 13 illustrates a face view of an embodiment of a button showing the first face.
Figure 14:
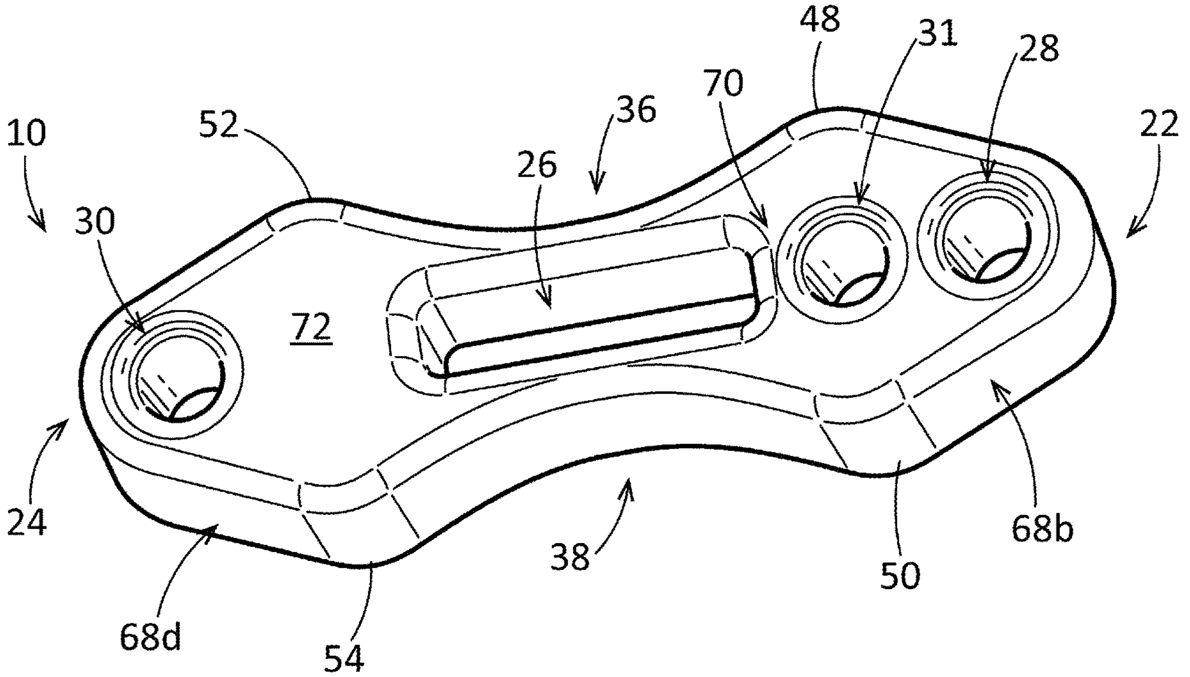
FIG. 14 illustrates a perspective view of a first face of an embodiment of a button.
Figure 15:
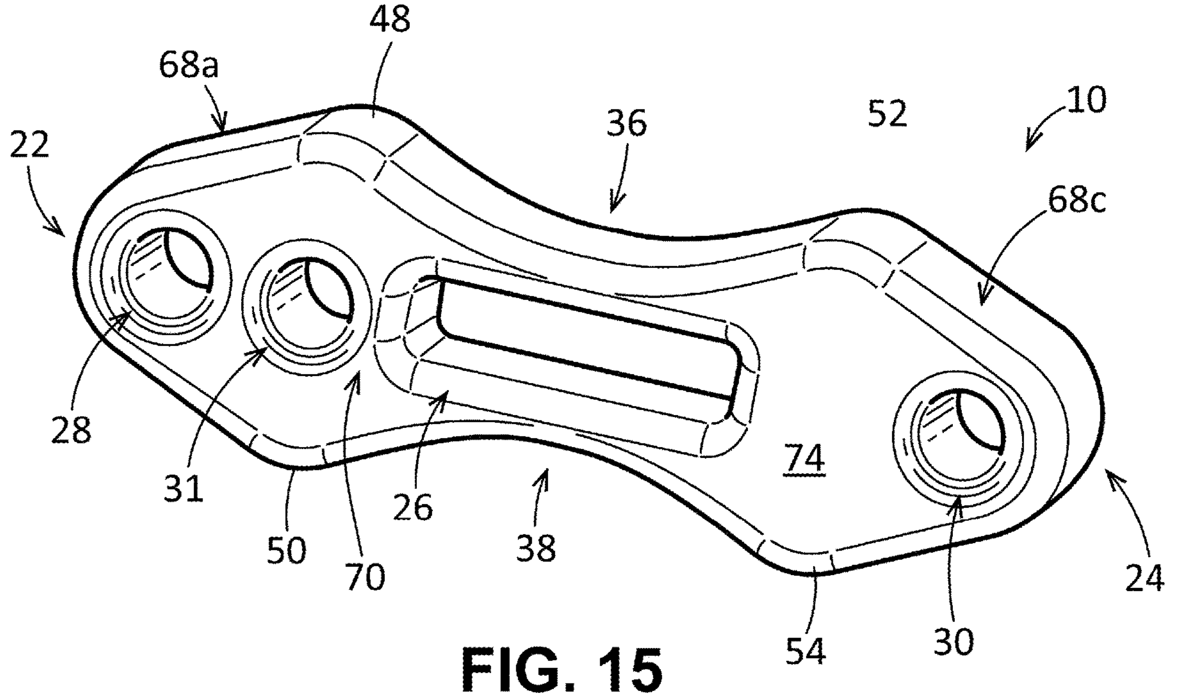
FIG. 15 illustrates a perspective view of a second face of an embodiment of a button.
Figure 16:
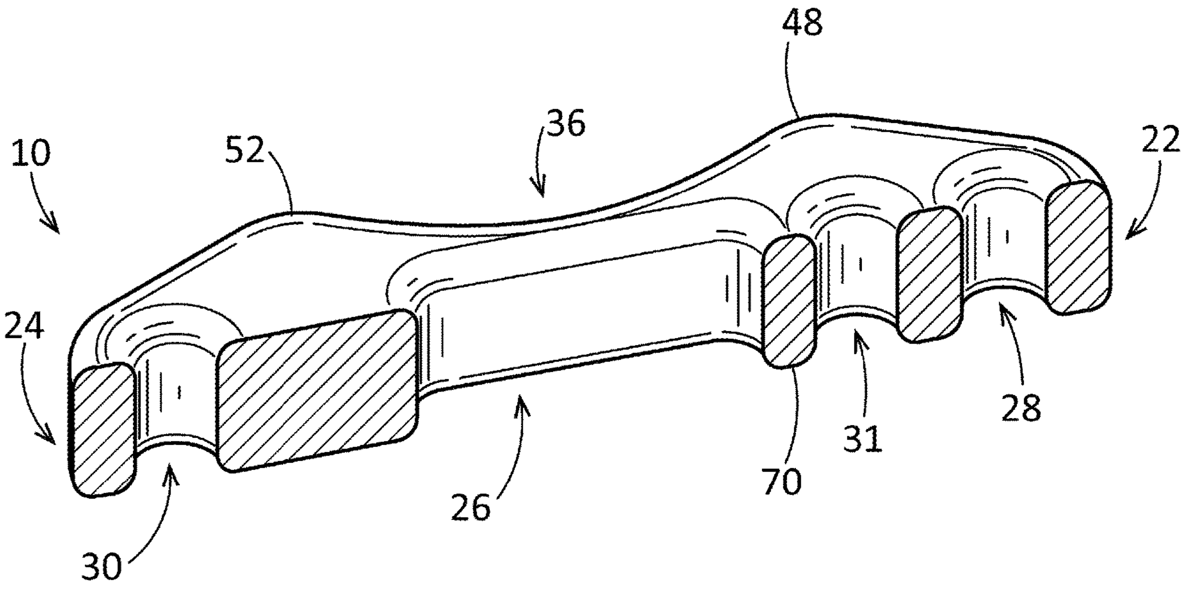
FIG. 16 illustrates a partial cross-sectional view of an embodiment of a button.

Referring to FIGS. 10-12, in some embodiments, button 10 includes a first face 72 and a second face 74 opposite first face 72. First and second faces 72, 74 each include a substantially flat planar surface between center passage 26, first hole 28 and second hole 30 in some embodiments. First end 22 is spaced relative to first end first shoulder 48 by first shoulder face **68*a* and spaced relative to first end second shoulder 50 by second shoulder face 68*b*. In some embodiments, first shoulder face 68*a* and second shoulder face 68*b* each include a substantially flat planar surface between the respective radii of curvature, forming a tapered profile toward first end 22. In alternative embodiments, first shoulder face 68*a* and second shoulder face 68*b* include a convex curvature Similarly, second end 24 is spaced relative to second end first shoulder 52 by third shoulder face 68*c* and spaced relative to second end second shoulder 54 by fourth shoulder face 68***d*. In some embodiments, third shoulder face 68*c* and fourth shoulder face 68*d* each include a substantially flat planar surface between the respective radii of curvature, forming a tapered profile toward second end 24. In alternative embodiments, third shoulder face 68*c* and fourth shoulder face 68*d* include a convex curvature.

As shown in FIG. 10 and FIG. 11, in some embodiments, a first recess 36 is defined as a concave recess in button 10 between first end first shoulder 48 and second end first shoulder 52. A first recess surface 37 includes a semi-cylindrical or semi-elliptical face forming a smooth, flat arc along the edge of button 10. First recess surface 37 is uninterrupted in some embodiments without any notch, groove, port or other indentation. In such embodiments, the concave profile of the first recess 36 between first end first shoulder 48 and second end first shoulder 52, both of which project outwardly away from first recess 36, allows a suture strand passing transversely around the button to slide into and seat in the first recess 36 against first recess surface 37.

Similarly a second recess 38 is defined as a concave recess in button 10 between first end second shoulder 50 and second end second shoulder 54. A second recess surface 39 includes a semi-cylindrical or semi-elliptical face forming a smooth, flat arc along the edge of button 10. Second recess surface 39 is uninterrupted in some embodiments without any notch, groove, port or other indentation. In such embodiments, the concave profile of the second recess 38 between second end first shoulder 50 and second end second shoulder 54, both of which project outwardly away from second recess 38, allows a suture strand passing transversely around the button to slide into and seat in the second recess 38 against second recess surface 39.

In some embodiments each hole opening, outer edge, and corner of button 10 is rounded with a radius cut or rounded edge to prevent wear or chafing of a suture material passing through, across or around button 10. In some embodiments, button 10 is polished to further enhance passage of suture material through, across or around button 10.

Referring to FIGS. 13-16, an alternative embodiment of button 10 includes a first hole 28 defined through button 10 between center passage 26 and first end 22. A second hole 30 is defined through button 10 between second end 24 and center passage 26. A third hole 31 is defined through button 10 between first hole 28 and center passage 26. Each hole includes a radius of curvature at the intersection of each hole opening and first and second faces 72, 74. The radius of curvature at each hole opening prevents chafing or wear on a suture passing through one or more holes. In some embodiments, third hole 31 is positioned closer to center passage 26 than first hole 28. In some embodiments first, second and third holes 28, 30, 31 each include the same hole diameter. In other embodiments, first second and third holes 28, 30, 31 include different hole diameters. Bridge 70 is defined between center passage 26 and third hole 31. Bridge 70 defines a structure over which a suture strand may be passed to provide an anchor point for a suture passing transversely to button 10.

Figure 17:
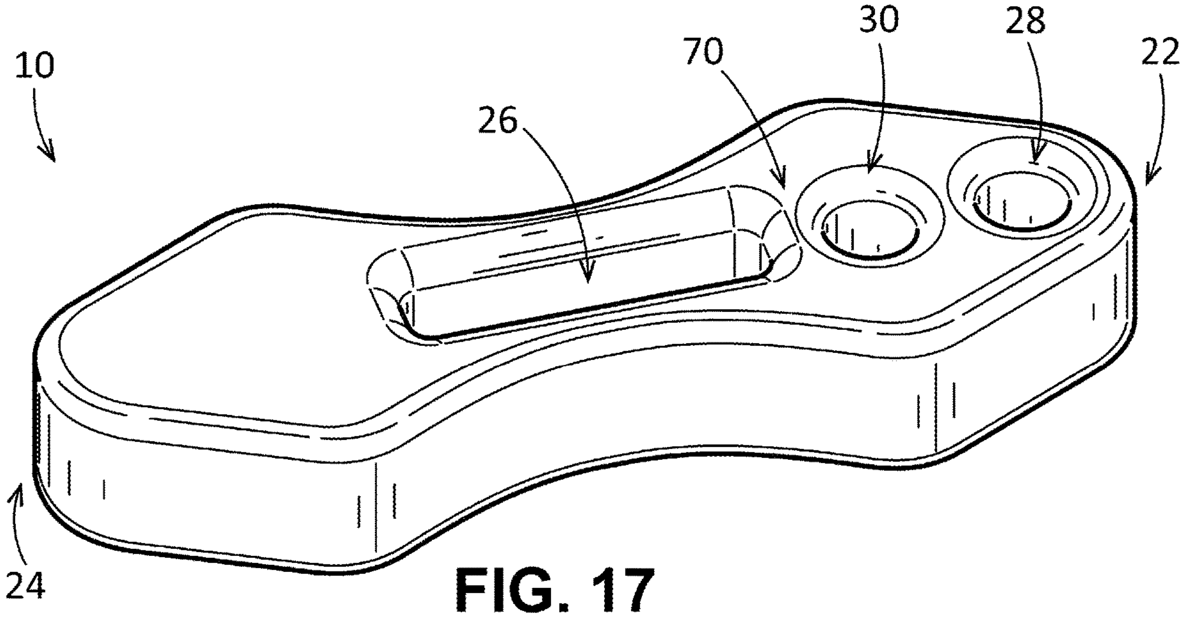
FIG. 17 illustrates a perspective view of a first face of an embodiment of a button.

Referring to FIG. 17, in some alterative embodiments, button 10 includes a first hole 28 defined through button 10 between center passage 26 and first end 22. A second hole 30 is defined through button 10 between first hole 28 and center passage 26. Each hole includes a rounded hole opening on each of first and second face 72, 74 of button to prevent chafing or wear of suture material passing through a hole. In some embodiments, no hole is defined between center passage 26 and second end 24.

Figure 18:
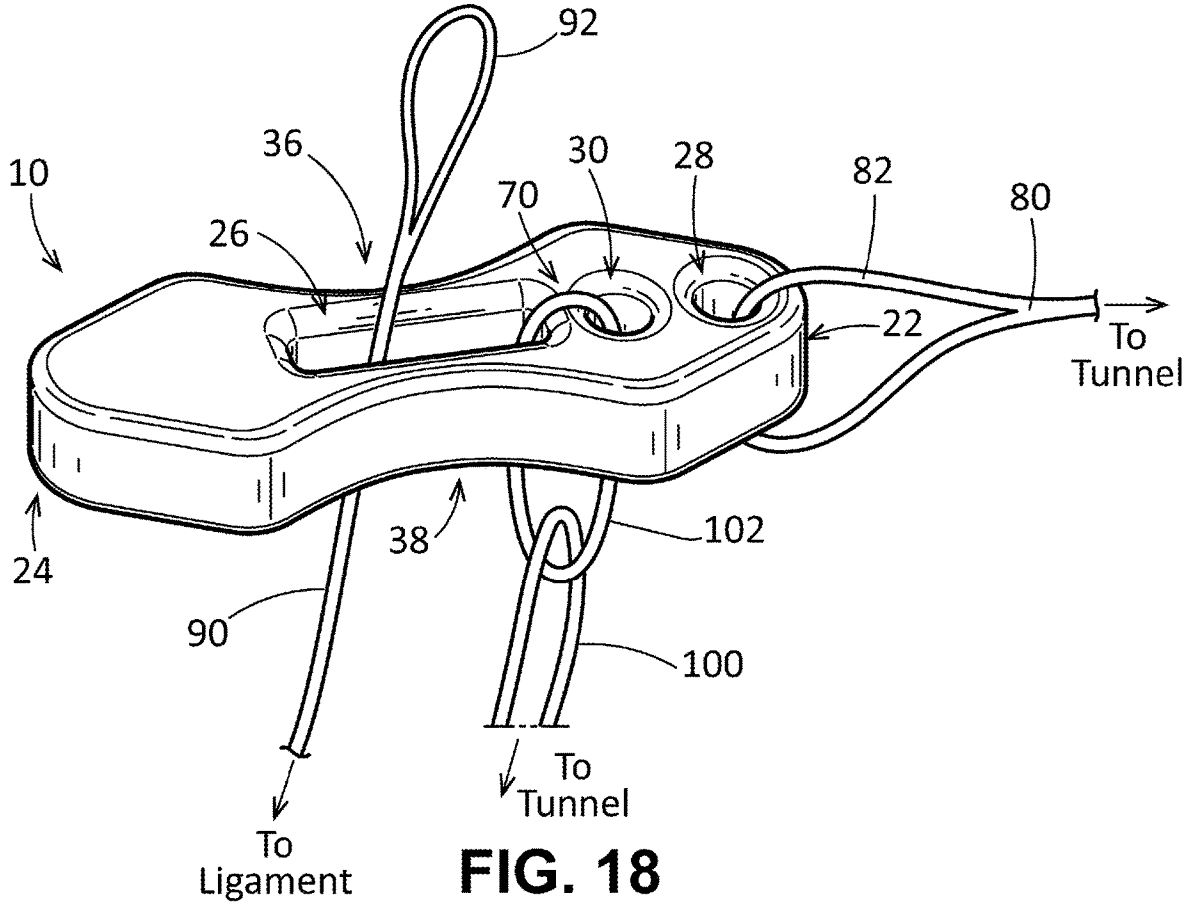
FIG. 18 illustrates a perspective view of an embodiment of a button including a passing suture, a ligament fixation suture construct and an internal brace suture construct.

Referring to FIG. 18, in some embodiments, button 10 is configured to provide an anchor for both a ligament fixation device 90 and an internal brace 100. In such embodiments, button 10 provides single fixation anchor for applying tension to a ligament during repair or reconstruction and also simultaneously applying tension for stabilizing a joint during healing of a ligament. For example, in some embodiments, ligament fixation device 90 may include a suture construct configured to be joined to a ligament such as a torn anterior cruciate ligament (ACL) at the distal end, and the proximal end of ligament fixation device 90 is passed through center passage 26. A ligament fixation device loop 92 is defined on the proximal end of the ligament fixation device 90. Similarly, internal brace 100 may include a static internal brace suture construct spanning from the button 10 through a femoral tunnel on the upper leg, across a knee joint, and through a tibal or fibial tunnel on the lower leg to a separate anchor to mechanically brace a knee joint during healing of the ACL. In some embodiments, a brace loop 102 is positioned around bridge 70 on button 10, and internal brace 100 is disposed on brace loop 102. Brace loop 102 in some embodiments includes a suture strand spliced at its ends around bridge 70, passing through center passage 26 and second hole 30 to form a continuous loop. In other embodiments using a button configuration shown in FIGS. 13-16, brace loop 102 is formed over bridge 70 by passing suture material through center passage 26 and third hole 31.

Figure 19:
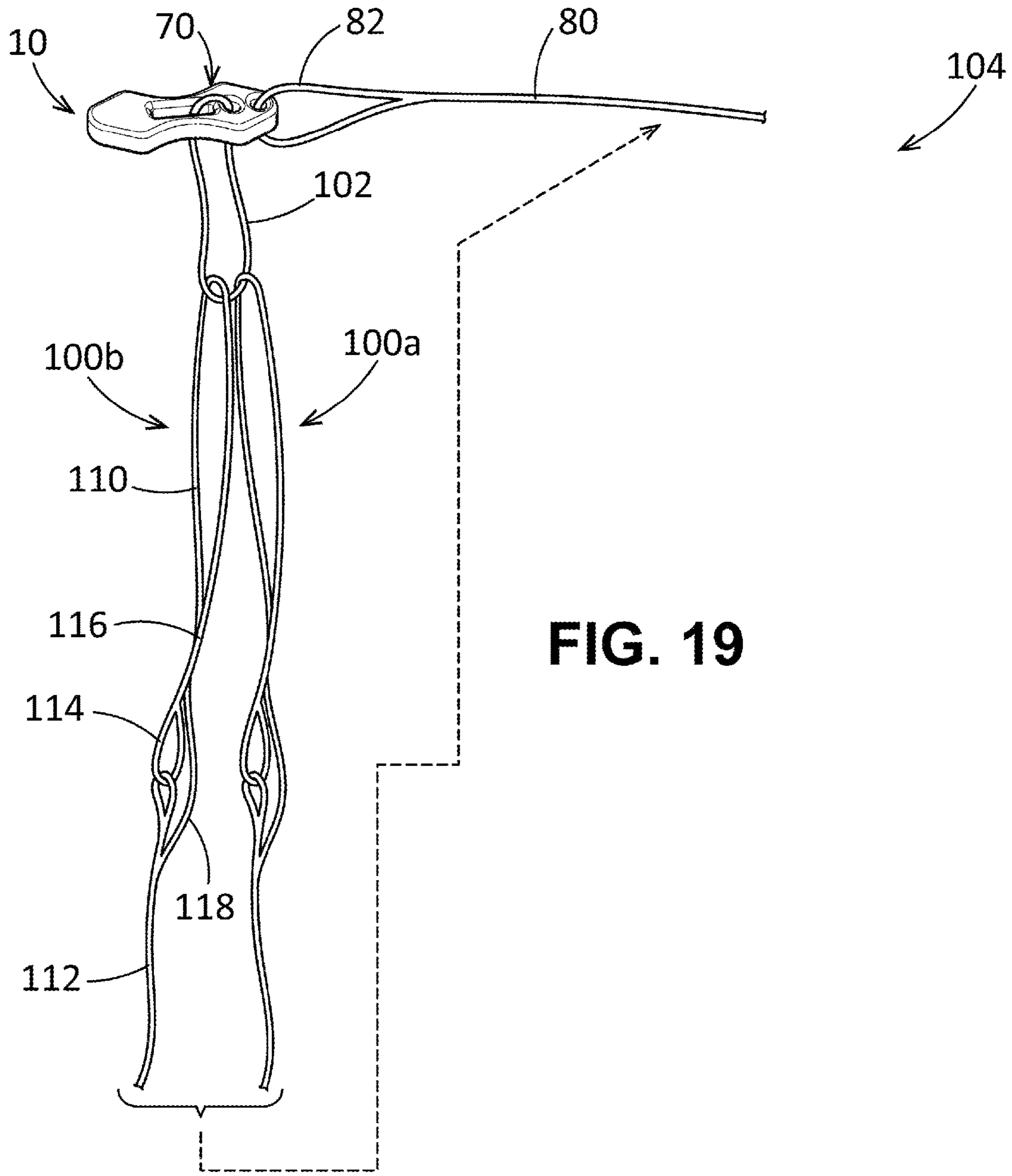
FIG. 19 illustrates a perspective view of an embodiment of a button including a passing suture and an internal brace suture construct.
Figure 20:
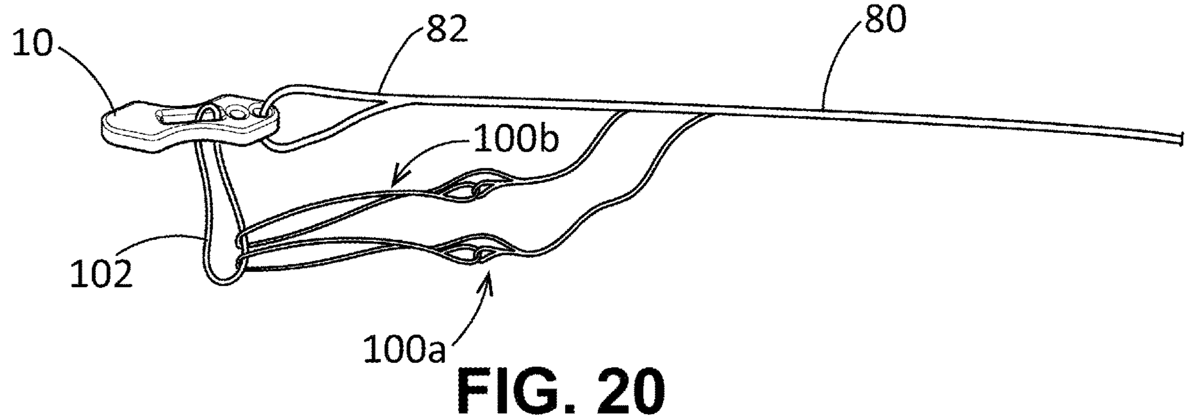
FIG. 20 illustrates a perspective view of an embodiment of a button including a passing suture and an internal brace suture construct.

Referring to FIG. 19 and FIG. 20, a brace apparatus 104 includes a button 10 with a passing suture 80, or shuttle suture, disposed on an end of the button 10 through the first hole. An internal brace construct is disposed on button 10 utilizing bridge 70. The internal brace construct includes a brace loop 102 and first and second internal brace constructs 100*a*, 100*b* in some embodiments. Each internal brace construct includes an adjustable self-cinching loop 110 with a brace passing suture 112 disposed on the distal end loop 114 of each construct in some embodiments. The self-cinching loop is formed by passing a strand of the internal brace construct through a portion of itself forming a self-cinching sleeve 116. A free end 118 of the strand may be removably inserted into its respective passing suture to temporarily secure the free end while passing the construct through a bone tunnel. From the configuration shown in FIG. 19, the end of each brace passing suture 112 may be temporarily inserted into or spliced into the passing suture 80 secured to button 10, as shown in FIG. 20.

Figure 21:
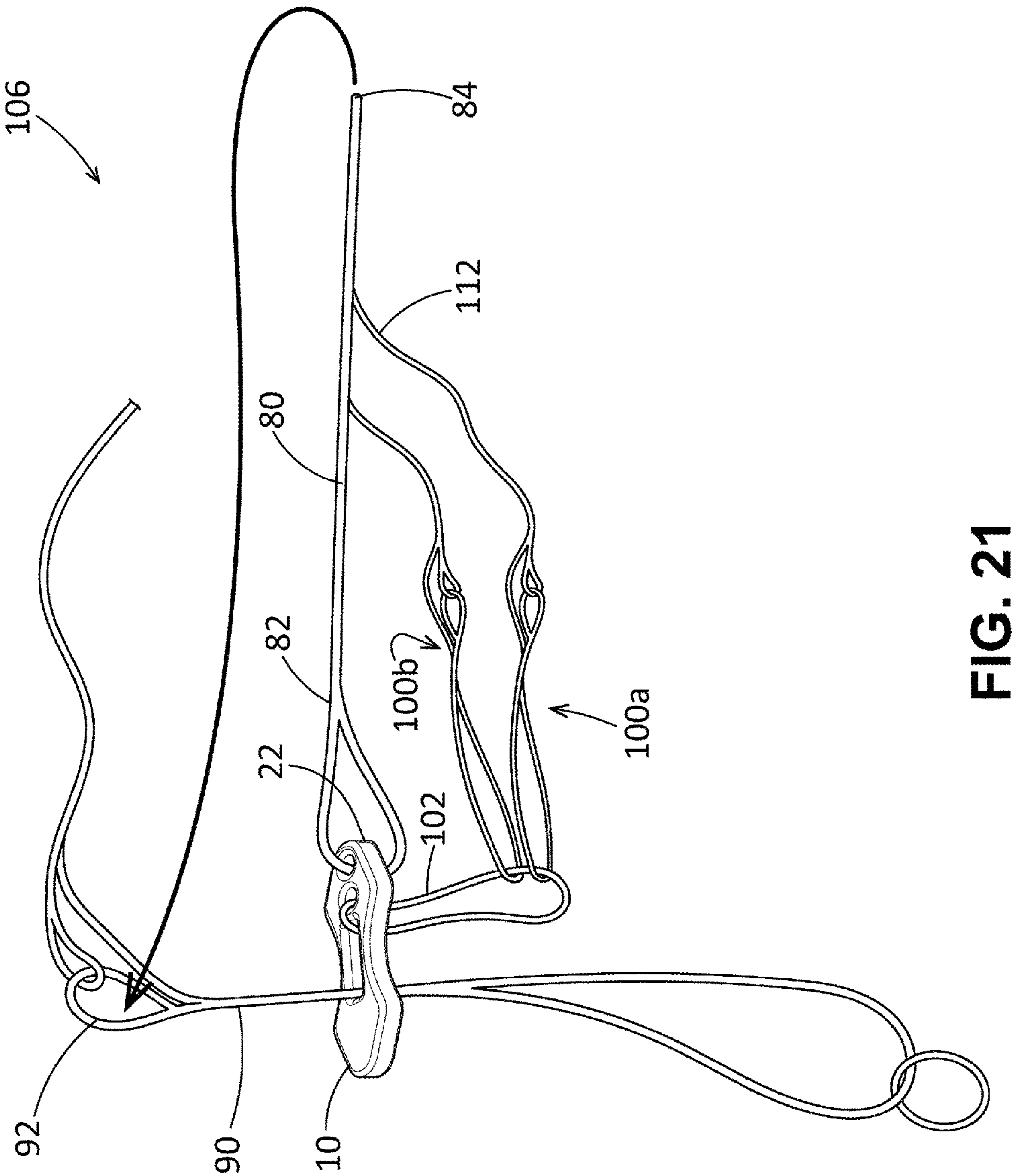
FIG. 21 illustrates a perspective view of an embodiment of a button including a passing suture, a ligament fixation suture construct and an internal brace suture construct positioned for forming a hitch around the button.
Figure 22:
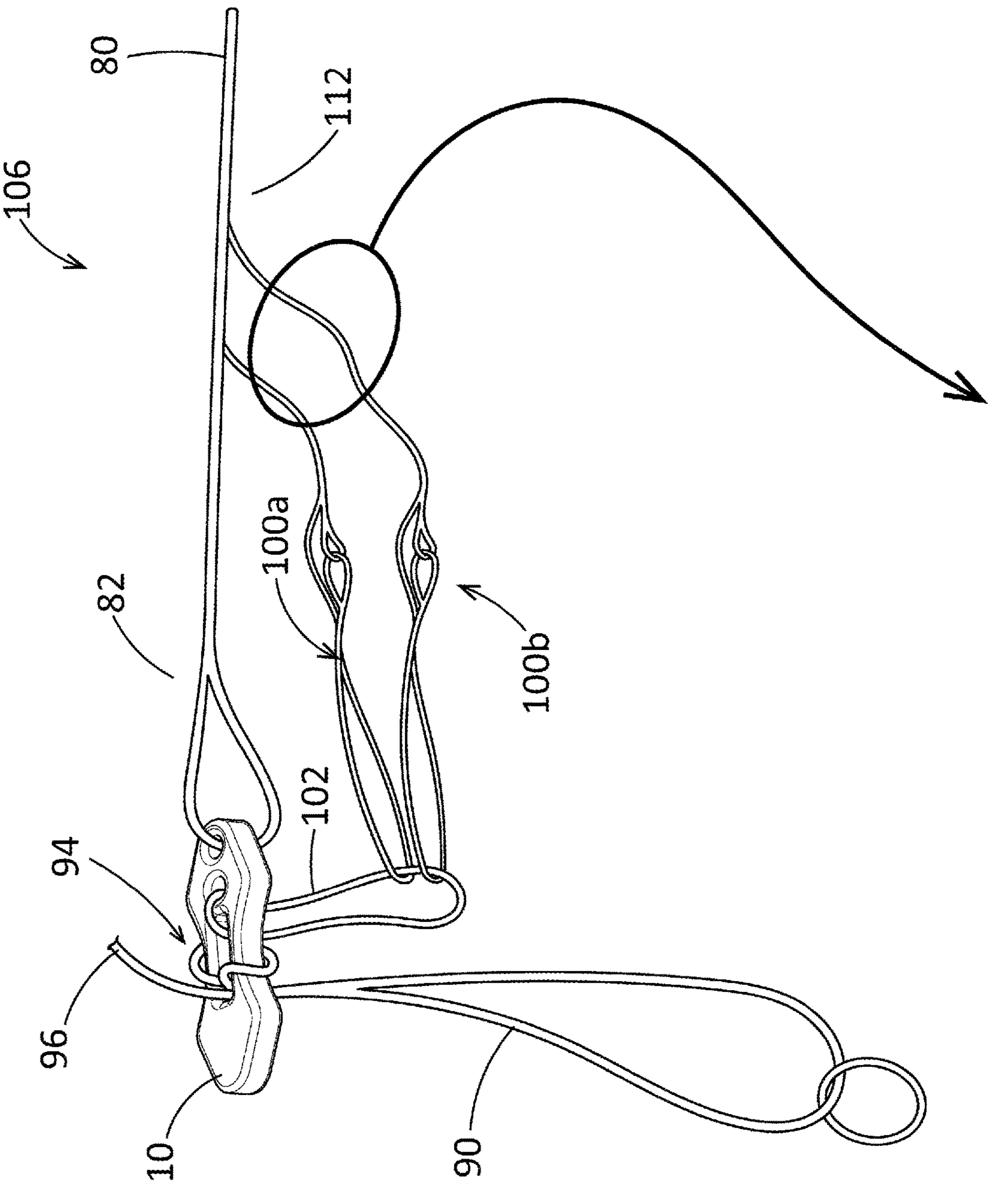
FIG. 22 illustrates a perspective view of an embodiment of a button including passing suture, a ligament fixation suture construct forming a hitch around the button, and an internal brace suture construct.
Figure 23:
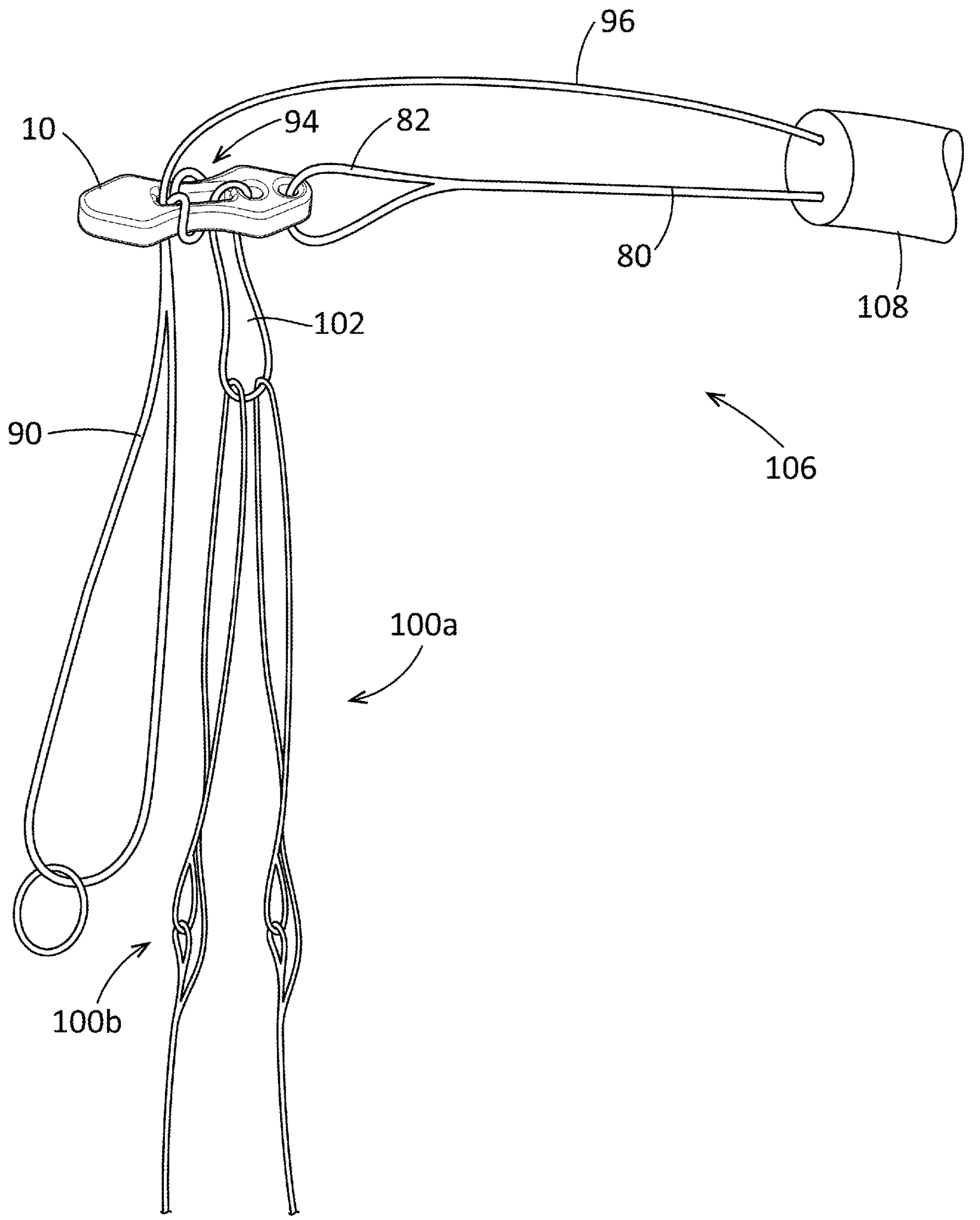
FIG. 23 illustrates a perspective view of an embodiment of a button including a passing suture, a ligament fixation suture construct, and an internal brace suture construct positioned for introduction into a bone tunnel.
Figure 24:
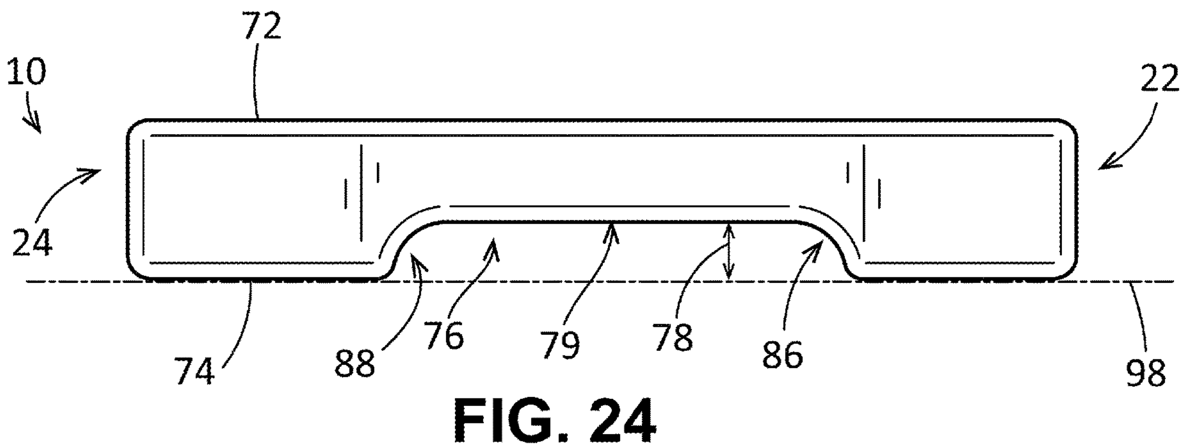
FIG. 24 illustrates an edge view of an embodiment of a button including a suture clearance recess defined in a face of the button.
Figure 25:
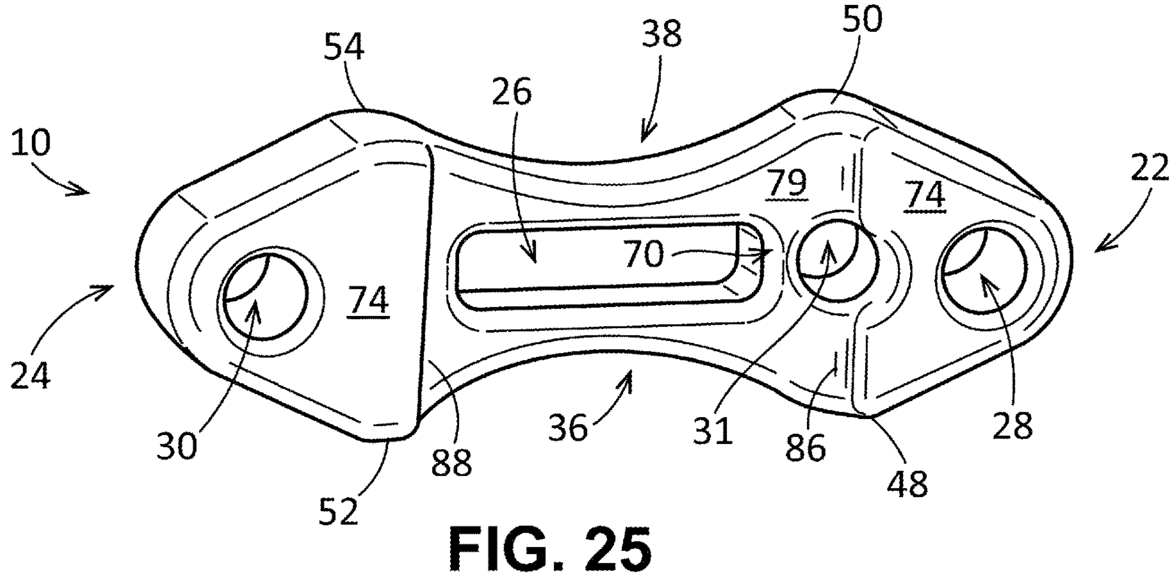
FIG. 25 illustrates a perspective view of an embodiment of a button including a suture clearance recess defined in a face of the button.
Figure 26:
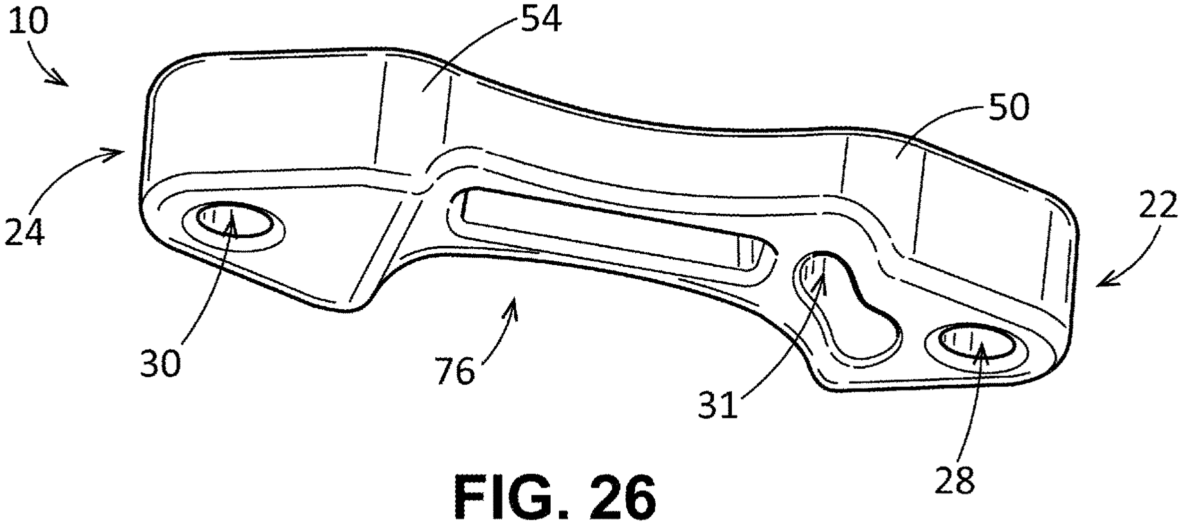
FIG. 26 illustrates a perspective view of an embodiment of a button including a suture clearance recess defined in a face of the button.
Figure 27:
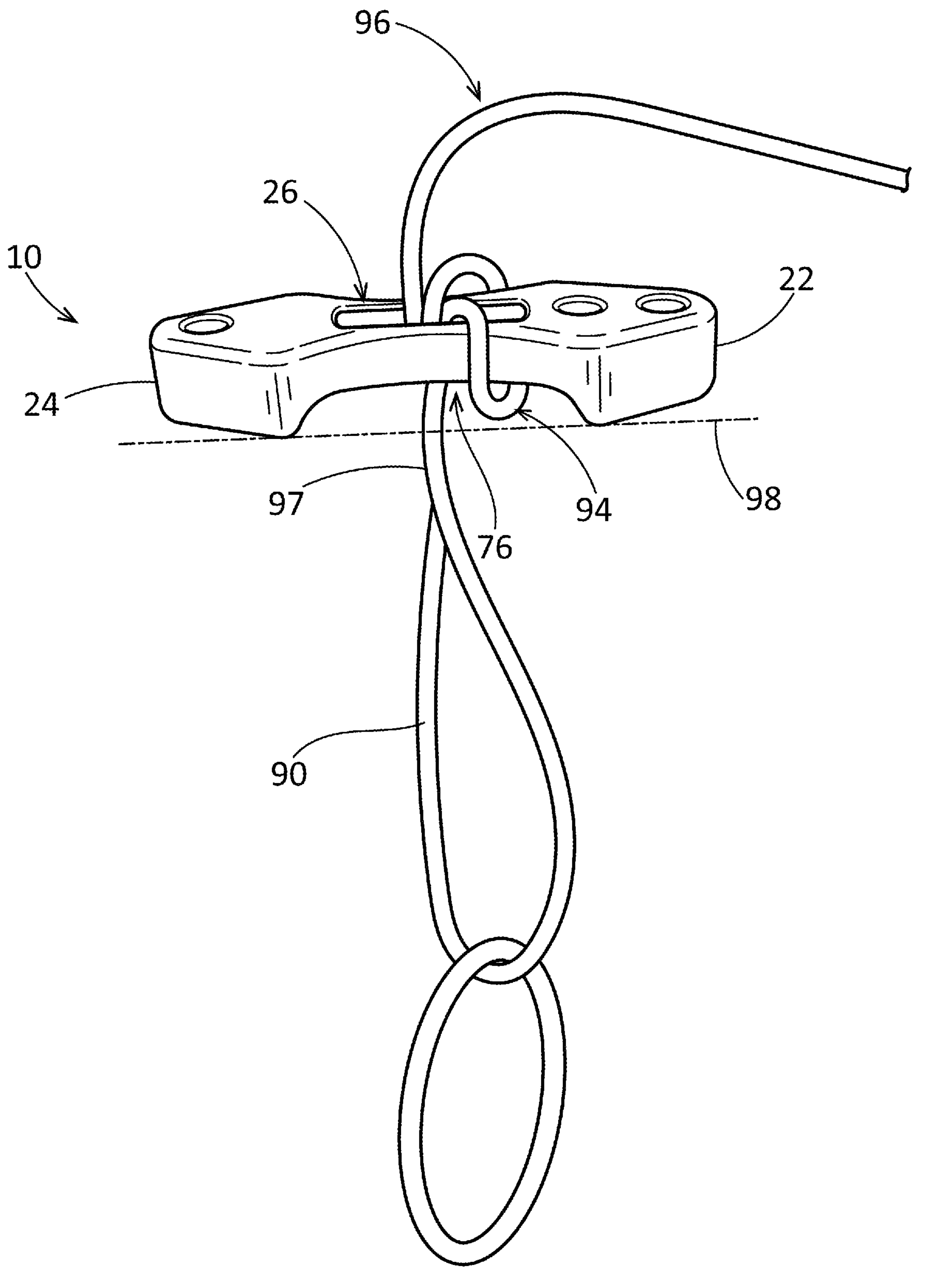
FIG. 27 illustrates a perspective view of an embodiment of a button including a suture clearance recess defined in a face of the button with a hitch formed around the button securing a suture construct to the button.

Referring to FIG. 21, a brace and repair apparatus 106 includes a button 10 with a passing suture 80 disposed on an end of the button 10 through the first hole. An internal brace construct is disposed on button 10 as discussed with respect to FIG. 19 and FIG. 20. In addition to the internal brace construct, a ligament fixation suture construct 90 is disposed through center passage 26 on button 10. The shuttling suture 80 with the ends of each brace passing suture 112 inserted into the passing suture 80 can be passed through a fixed loop 92 on the end of the ligament fixation suture construct 90 and pulled to pass the fixed loop 92 over the entirety of the shuttling suture 80 and also the first and second internal brace constructs 100*a*, 100*b* and the brace loop 102 to form a hitch around button 10 by fixed loop 92. As such, fixed loop 92 is seated in first recess 36 and second recess 38 on button 10, as shown in FIG. 22. From this position, the first and second ends of brace passing suture 112 on first and second internal brace constructs 100*a*, 100*b* can be removed from passing suture 80 and positioned for passage through anatomy, as shown in FIG. 23. In some embodiments, each brace passing suture 112 may be inserted through a bridge enhanced ACL restoration (BEAR) implant or other intermediate device and finally secured to an anchor on the tibia at the distal end. From this position, the repair or reconstruction construct 90 is anchored to button 10 via hitch 94, and first and second internal brace constructs 100*a*, 100*b* are anchored to button 10 via brace loop 102 which is joined to bridge 70. At this point, a free end 96 of the ligament fixation suture construct 90 may be passed through a bone tunnel, such as a femoral tunnel, 108. Additionally, passing suture 80 may also be passed through the tunnel 108, and button 10 may be pulled through the tunnel using passing suture 80. Once the anchor is pulled through the tunnel, the button 10 may be flipped such that the button lays flat against the bone on the opposite end of the tunnel to secure the button in place.

Referring to FIGS. 24-27, an alternative embodiment of button 10 includes a suture clearance recess 76 defined in second face 74 between first end 22 and second end 24. In some embodiments, suture clearance recess 76 is defined in second face 74 between first hole 28 and second hole 30. Suture clearance recess 76 is defined in button 10 is a blind recess extending from a first lateral edge of button 10 to the opposite lateral edge of button 10. Suture clearance recess 76 includes a recess depth 78 dimensioned to accommodate a suture material thickness in the recess such that the suture material does not extend beyond the second face plane 98 when a hitch is formed around button 10.

Figure 28:
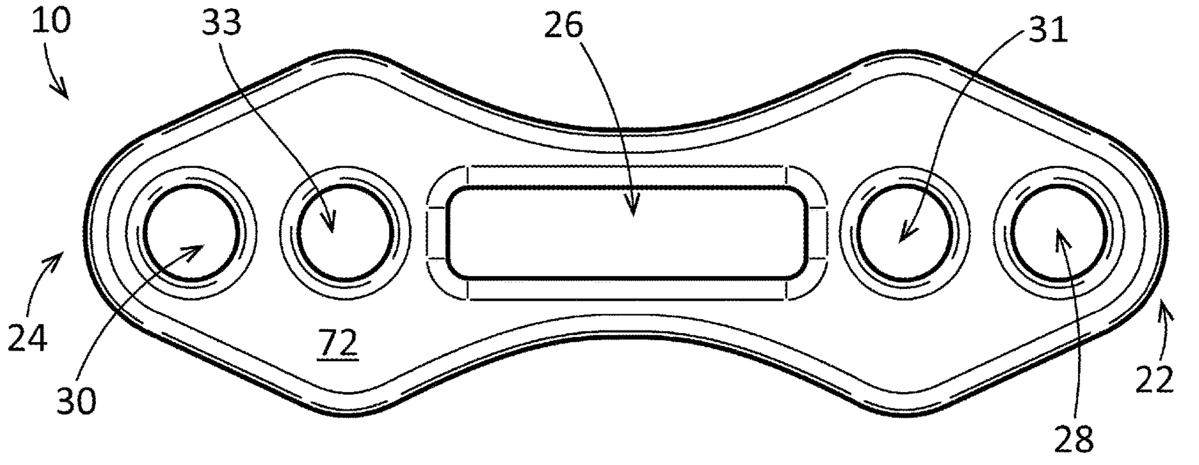
FIG. 28 illustrates a first face view of an embodiment of a button.
Figure 29:
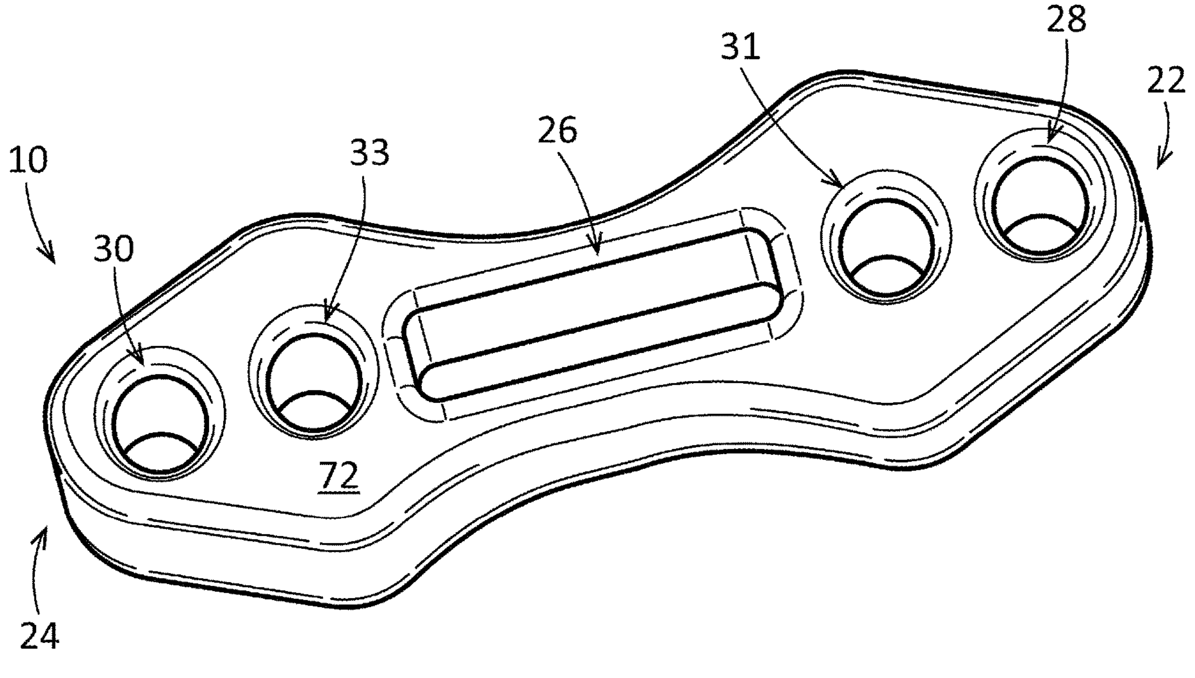
FIG. 29 illustrates a perspective view of a first face of an embodiment of a button.
Figure 30:
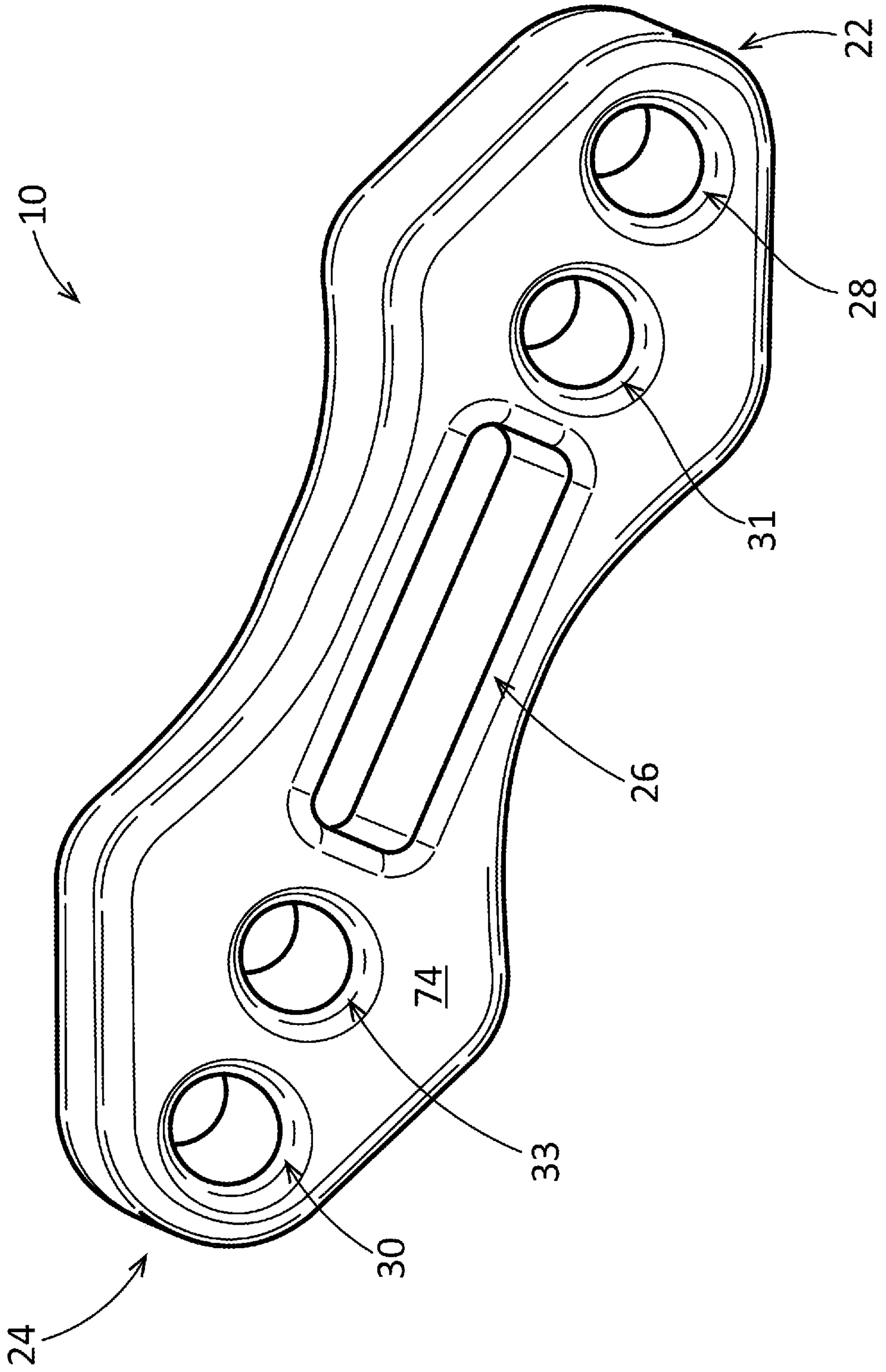
FIG. 30 illustrates a perspective view of a second face of an embodiment of a button.

Referring to FIGS. 28-30, in some additional embodiments, button 10 includes a configuration including a center passage 26, a first hole 28 defined through the button 10 between center passage 26 and first end 22, a second hole 30 defined through the button 10 between center passage 26 and second end 24, a third hole 31 defined through button 10 between center passage 26 and first hole 28, and a fourth hole 33 defined between center passage 26 and second hole 30. Each hole includes a clearance hole defined entirely through the body of button 10. Each hole includes a rounded hole opening on each of the first and second faces 72, 74 of button 10 to prevent chafing or wear of a suture material passing through the hole. First, second, third and fourth holes 28, 30, 31, 33 may be configured to accept one or more suture constructs such as passing sutures, ligament fixation suture constructs, continuous loop suture constructs, toggle sutures, or internal brace suture constructs.

Figure 31:
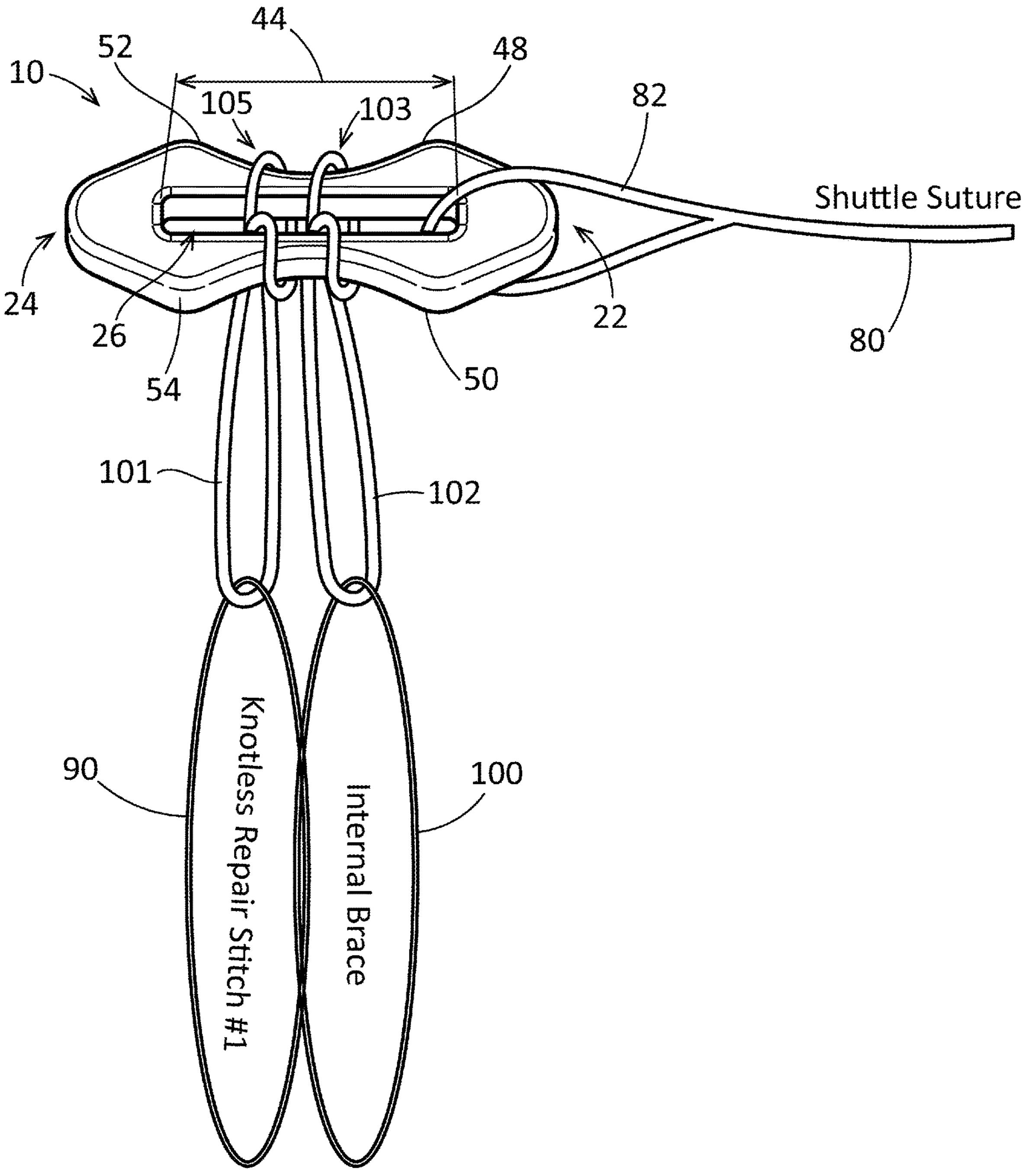
FIG. 31 illustrates a perspective view of an embodiment of a button with an elongated center passage configured for attaching a ligament fixation construct and an internal brace construct and a shuttle suture to the button via the center passage.

Referring to FIG. 31, in some embodiments, button 10 includes an elongated center passage 26 such that the center passage length 44 is greater than the distance between first end first shoulder 48 and second end first shoulder 52. Additionally, the center passage length 44 is greater than the distance between first end second shoulder 50 and second end second shoulder 54. As such, the elongated center passage 26 provides additional space for attachment of an internal brace suture construct 100 and a ligament fixation suture construct 90. In some embodiments, a first continuous loop 101 is formed in a first hitch 105 around button 10 such that the loop extends through the center passage 26. A ligament fixation suture construct 90, such as a knotless repair stitch, is disposed on the portion of the first continuous loop 101 extending through the center passage 26. Similarly, a second continuous loop 102 is formed in a second hitch 103 around button 10 such that the loop extends through the center passage 26. An internal brace suture construct 100 is disposed on the portion of the second continuous loop 102 extending through the center passage 26. Also, a shuttling suture, or passing suture 80 is disposed on button 10. In some embodiments, passing suture 18 includes a fixed loop 82 extending through center passage 26 and extending from first end 22. The fixed loop 82 may be formed by splicing a strand of suture material into itself after passing through center passage 26. Similarly, first and second continuous loops 101, 102 may each be formed of a strand of suture material spliced together at the ends to form a continuous ring prior to forming the respective continuous loop hitches around button 10. As shown in FIG. 31, in some embodiments, the internal brace suture construct 100 is disposed between the ligament fixation suture construct 90 and the passing suture 80. In alternative embodiments, this configuration may be reversed such that the ligament fixation suture construct 90 is disposed between internal brace suture construct 100 and passing suture 80.

Thus, although there have been described particular embodiments of the present invention of a new and useful SUTURE BUTTON AND METHODS, it is not intended that such references to particular embodiments be construed as limitations upon the scope of this invention.

What is claimed is:

1. A suture button apparatus, comprising:

a body including a first end, a second end, a first side and a second side;

a first recess defined in the first side;

a second recess defined in the second side;

a center passage defined through the body between the first end, the second end, the first side and the second side;

a first hole defined through the body between the center passage and the first end; and a second hole defined through the body between the center passage and the first hole, the second hole centered on a longitudinal midline of the body, wherein the center passage is disposed on a lateral midline of the body, and wherein the first recess and second recess each form an uninterrupted arc.

2. The apparatus of claim 1, wherein the body includes a longitudinal dimension greater than a lateral dimension.

3. The apparatus of claim 1, wherein:

the first recess includes a first side radius bottoming toward the center passage along the lateral midline; and the second recess includes a second side radius bottoming toward the center passage along the lateral midline.

4. The apparatus of claim 1, wherein the center passage includes a rectangular profile.

5. The apparatus of claim 4, wherein the center passage includes a center passage length and a center passage width, wherein the center passage length is greater than the center passage width.

6. The apparatus of claim 5, wherein the center passage width is substantially equal to the diameters of the first and second holes.

7. The apparatus of claim 1, further comprising a first end first shoulder on the first side and a first end second shoulder on the second side opposite the first end first shoulder.

8. The apparatus of claim 7, further comprising a second end first shoulder on the first side and a second end second shoulder on the second side opposite the second end second shoulder.

9. The apparatus of claim 8, further comprising:

a convex radius on the body between the first end and the first end first shoulder on the first side;

a convex radius on the body between the first end and the first end second shoulder on the second side;

a convex radius on the body between the second end and the second end first shoulder on the first side; and a convex radius on the body between the second end and the second end second shoulder on the second side.

10. The apparatus of claim 8, further comprising:

a substantially flat planar surface on the body between first end and the first end first shoulder on the first side;

a substantially flat planar surface on the body between the first end and the first end second shoulder on the second side;

a substantially flat planar surface on the body between the second end and the second end first shoulder on the first side; and a substantially flat planar surface on the body between the second end and the second end second shoulder on the second side.

11. The apparatus of claim 1, wherein:

the first end includes a tapered profile having a first end radius on the first end; and the second end includes a tapered profile having a second end radius on the second end.

12. The apparatus of claim 1, wherein the first recess and the second recess are both centered along the lateral midline of the body.

13. The apparatus of claim 1, further comprising a bridge defined between the center passage and the second hole.

14. The appartus of claim 1, wherein the center passage is centered on the lateral midline.

15. A suture button apparatus, comprising:

a suture button body including a first end, a second end, a first side recess and a second side recess;

a center passage defined through the suture button body between the first and second side recesses;

a first hole defined through the suture button body between the center passage and the first end; and a second hole defined through the suture button body between the center passage and the first hole, the second hole centered on a longitudinal midline of the suture button body, wherein the center passage is disposed on a lateral midline of the suture button body.

16. The apparatus of claim 15, further comprising:

a ligament fixation suture construct disposed on the suture button body, wherein a portion of the ligament fixation suture construct is disposed around the suture button body in the first and second side recesses.

17. The apparatus of claim 16, further comprising:

an internal brace suture construct disposed on the suture button body, wherein a portion of the internal brace suture construct extends through both the center passage and one of the first and second holes.

18. The apparatus of claim 17, further comprising:

a passing suture disposed on the suture button body separate from the ligament fixation suture construct and the internal brace suture construct.

19. The apparatus of claim 15, wherein the center passage is centered on the lateral midline.

* * * * *